United States Patent
Sinha et al.

(10) Patent No.: US 12,240,818 B2
(45) Date of Patent: Mar. 4, 2025

(54) CRYSTALLINE FORMS OF PLASMA KALLIKREIN INHIBITORS

(71) Applicants: Rezolute, Inc., Redwood City, CA (US); ActiveSite Pharmaceuticals, Inc., San Francisco, CA (US)

(72) Inventors: Sukanto Sinha, San Francisco, CA (US); Tamie Chilcote, San Francisco, CA (US); Julian Scott Northen, South Shields (GB); Jamie Marshall, Gateshead (GB)

(73) Assignees: Rezolute, Inc., Redwood City, CA (US); ActiveSite Pharmaceuticals, Inc., San Francisco, CA (US)

( * ) Notice: Subject to any disclaimer, the term of this patent is extended or adjusted under 35 U.S.C. 154(b) by 245 days.

(21) Appl. No.: 17/694,543

(22) Filed: Mar. 14, 2022

(65) Prior Publication Data

US 2022/0380315 A1 Dec. 1, 2022

Related U.S. Application Data

(62) Division of application No. 16/922,064, filed on Jul. 7, 2020, now Pat. No. 11,306,061.

(60) Provisional application No. 62/871,517, filed on Jul. 8, 2019.

(51) Int. Cl.
*C07D 231/14* (2006.01)

(52) U.S. Cl.
CPC ........ *C07D 231/14* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,627,646 B2 | 9/2003 | Bakale et al. |
| 8,258,170 B2 | 9/2012 | Sinha et al. |
| 8,259,170 B2 | 9/2012 | Salisbury et al. |
| 8,658,685 B2 | 2/2014 | Aiello et al. |
| 10,246,418 B2 | 4/2019 | Chen et al. |
| 11,306,061 B2 | 4/2022 | Sinha et al. |

FOREIGN PATENT DOCUMENTS

| | | |
|---|---|---|
| WO | 2007070589 | 6/2007 |
| WO | 2008016883 | 7/2008 |
| WO | 2010065656 | 6/2010 |
| WO | 2019/106377 | 6/2019 |

OTHER PUBLICATIONS

Bernstein, "Polymorphism in Molecular Crystals". Dept. of Chem. Ben-Gurion Univ. p. 115-118, 272 (2002).

Davidovich et al., "Detection of polymorphism by Powder X-Ray Diffraction: Interference by Preferred Orientation" Am. Pharm. Rev. v.(1) p. 10, 12, 14, 16, 100 (2004).
Dean, John A. "Analytical Chemistry Handbook" p. 10.24-10.26 (1995).
Ivanisevic et al. "Use of X-ray Powder Diffraction in the Pharmaceutical Industry". Pharnn. Sci. Encycl. p. 1-42 (2010).
Seddon "Pseudopolymorph: A Polemic" Crystal Growth & Design, v.4(6) p. 1087 (2004) (2 pages).
Rodriguez-Spong et al., "General principles, etc.," Adv. Drug Delivery Reviews 56 (2004) 241-274.
Kirk-Othmer Encyclopedia of Chemical Technology, 8, pp. 95-147 (2002).
Vippagunta et al., "Crystalline Solids", Advanced Drug Delivery Reviews 48 (2001) 3-26.
Guillory (in Brittain ed.), "Polymorphism in Pharmaceutical Solids.," NY: Marcel Dekker, Inc., 1999, 1-2, 183-226.
Braga et al., "Making crystals from crystals: a green route to crystal engineering and polymorphism" J. Royal Soc. Chem. Commun. p. 3635-3645 (2005).
CMU Seed Fund Project on Detection and Control of Pharmaceutical polymorphism, internet p. 1-3 (2002) printout. Accessed Apr. 3, 2008.
Singhal et al., "Drug Polymorphism, etc.," Advanced Drug Delivery reviews 56, p. 335-347 (2004).
Concise Encyclopedia Chemistry, NY: Walter de Gruyter, 1993, 872-873.
Jain et al., "Polymorphism in Pharmacy", Indian Drugs, 1986, 23(6) 315-329.
Muzaffar et al., "Polymorphism and Drug Availability". J of Pharm. (Lahore), 1979, 1(1), 59-66.
U.S. Phamnacopia #23, National Formulary #18, 1995, 1843-1844.
Doelker. E. , English translation of "Physicochemical Behaviors of Active Substances their Consequences for the Feasibility and the Stability of Pharmaceutical forms". S.T.P, Pratiques (1999), 9(5), 399-409, pp. 1-33.
Doelker, English translation of "Crystalline Modifications and Polymorphous Changes During Drug Manufacture". Ann. Pharm. Fr., 2002, 60: 161-176, pp. 1-39.
Taday et al., "Using Terahertz, etc.," J of Pharm. Sci., 92(4), 2003, 831-838.

(Continued)

*Primary Examiner* — Zinna Northington Davis
(74) *Attorney, Agent, or Firm* — Mintz, Levin, Cohn, Ferris, Glovsky and Popeo, P.C.

(57) ABSTRACT

Pure crystalline forms of 1-benzyl-N-(4-carbamimidoylbenzyl)-1H-pyrazole-4-carboxamide acetate, and an amorphous form, pharmaceutical compositions thereof, and methods for making the same, are disclosed.

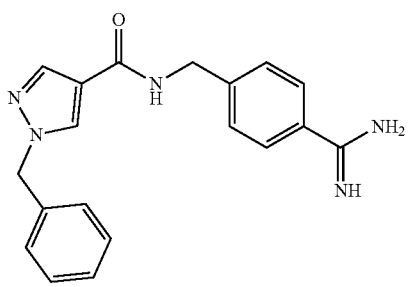

11 Claims, 12 Drawing Sheets

(56) References Cited

OTHER PUBLICATIONS

Otuska et al., "Effect of Polymorphic Forms of Bulk Powders on Pharmaceutical Properties of Carbamazepine Granules.," Chem. Pharm. Bull., 47(6) 852-856 (1999).

Byrn et al., "Pharmaceutical Solids: A Strategic Approach to Regulatory Considerations" Pharma Research, vol. 12, pp. 945-954. (1995).

Pubchem, Substance record for SID 224511546, Available Date: Feb. 2, 2015 (retrieved Sep. 11, 2020).

Richard J. Bastin et al., "Salt selection and Optimisation Procedures for Pharmaceutical New Chemical Entities", Organic Process Research & Development, 2000, vol. 4, pp. 427-435.

Sarma B. et al., "Solid formation of pharmaceuticals: Polymorphs, salt and cocrystals", Korean J. Chem. Eng., 2011, vol. 28(2), pp. 315-322 (p. 317 section of "Pharmaceutical salts", paragraph 1 to p. 319 left column).

Mino R. Caira, "Crystalline Polymorphism of Organic Compounds", Topics in Current Chemistry, 1998, vol. 198, pp. 163-208 (p. 164, section 3.1).

Gupta, D. et al., Salts of Therapeutic Agents: Chemical, Physicochemical, and Biological Considerations. Molecules, Jul. 14, 2018, vol. 23, No. 7, pp. 1719 Section 2.6, table 1, the 3rd sentence in section 2.8, section 3.3.

CRYSTALLINE FORMS OF PLASMA KALLIKREIN INHIBITORS

CROSS-REFERENCES TO RELATED APPLICATIONS

This application is a divisional of U.S. patent application Ser. No. 16/922,064, filed Jul. 7, 2020, which claims the benefit of priority under 35 U.S.C. § 119(e) to U.S. Provisional Application Ser. No. 62/871,517 filed Jul. 8, 2019, the disclosures of each are incorporated herein by reference in their entirety.

FIELD OF THE INVENTION

This invention relates to crystalline forms of plasma kallikrein inhibitors, methods of making polymorphs of plasma kallikrein inhibitors that are substantially free of other polymorphs, and compositions comprising a substantially pure polymorph of plasma kallikrein inhibitors.

BACKGROUND OF THE INVENTION

Thrombus formation is essential for preventing blood loss and allowing repair of an injured vessel, a process known as hemostasis, yet a thrombus can also be pathologic when it occludes a blood vessel and deprives tissue of oxygen. The occlusion of an artery by a thrombus, arterial thrombosis, most often occurs at the site of a ruptured or eroded atherosclerotic plaque (V. Kou et al., *Mt Sinai J Med* (2006) 73:449-68). Specific occlusion of coronary arteries results in acute coronary syndrome, which includes unstable angina and myocardial infarction (MI).

A fibrin clot may be produced in blood by initiation of either of two distinct routes, the intrinsic and extrinsic pathways, which converge onto a common pathway of coagulation (R. G. Macfarlane, *Nature* (1964) 202:498-99; E. W. Davie et al., *Science* (1964) 145:1310-12; K. Joseph et al., *Adv Immunol* (2005) 86:159-208). Experimental data have suggested both plasma kallikrein (PK) deficient and Factor XII (FXII) deficient individuals have severely impaired intrinsic pathway-mediated clot formation despite their lack of bleeding phenotype (O. D. Ratnoff et al., *J Clin Invest* (1955) 34:602-13; R. W. Colman, (2001) in "Hemostasis and Thrombosis: Basic Principles and Clinical Practice" (R. W. Colman et al., eds., Lippincott, Williams & Wilkins, Philadelphia, Pa., pp. 103-122); E. D. Rosen et al., *Nature* (1997) 390:290-94; W. E. Hathaway et al., *Blood* (1965) 26:521-32; A. S. Lawrie et al., *Clin Lab Haematol* (1998) 20:179-86; and S. M. Bates et al., *Circulation* (2005) 112:53-60). In the intrinsic pathway, by binding to the surface, a small amount of FXII is activated (FXIIa), which in turn activates PK through proteolysis. Importantly, PK then generates additional FXIIa in a feedback loop, which in turn activates factor XI (FXI) to FXIa and connects to the common pathway. Although the initial activation of the intrinsic pathway is through a small amount of FXIIa activating a small amount of PK, it is the subsequent feedback activation of FXII by PK that controls the extent of activation of the intrinsic pathway, and hence downstream coagulation (W. E. Hathaway et al., *Blood* (1965) 26:521-32).

Current treatment for acute MI or ischemic stroke in a hospital setting requires emergency measures to dissolve the occluding thrombus and allow reperfusion (restored blood flow). One of the common ways of doing this is by treating the patients with fibrinolytic agents, such as tissue plasminogen activator (t-PA) or streptokinase, agents that lead to the generation of active plasmin from plasminogen. Plasmin cleaves the fibrin meshwork of the thrombus, leading to clot dissolution. Such fibrinolytic agents are the most frequently used treatment for reperfusion worldwide. However, fibrinolysis is also associated with a high degree of re-thrombosis with subsequent rates of reocclusion of up to 50% depending on the study (F. Zijlstra et al., *N Engl J Med* (1993) 328:680-84; B. R. Brodie et al., *Circulation* (1994) 90:156-62; G. W. Stone et al., *Circulation* (1999) 99:1548-54; H. Tamai et al., *Am Heart J* (2004) 147:E9; F. W. Verheugt et al., *J Am Coll Cardiol* (1996) 27:766-73).

Patients who have experienced acute MI show clinical evidence of being in a hypercoagulable (clot-promoting) state. This hypercoagulability is paradoxically additionally aggravated in those receiving fibrinolytic therapy. Increased generation of thrombin, as measured by thrombin-antithrombin III (TAT) levels up to 2-fold higher, is observed in patients undergoing such treatment, relative to the already high levels observed in those receiving heparin alone (H. M. Hoffmeister et al., *Circulation* (1998) 98:2527-33). The increase in thrombin has been proposed to result from plasmin-mediated activation of the intrinsic pathway. Plasmin-mediated activation of the intrinsic pathway system is known to occur in blood (G. A. Ewald et al., *Circulation* (1995) 91:28-36), and it has been suggested that this occurs as a consequence of direct activation of FXII by plasmin.

Not only does the fibrinolysis-induced hypercoagulability lead to increased rates of reocclusion, it is also probably responsible, at least in part, for failure to achieve complete fibrinolysis of the clot, a major shortcoming of fibrinolytic therapy (E. C. Keeley et al., *Lancet* (2003) 361:13-20). Another problem in fibrinolytic therapy is the accompanying 3-fold elevated risk of intracranial hemorrhage (ICH) (V. Menon et al., *Chest* (2004) 126:549S-575S; Fibrinolytic Therapy Trialists' Collaborative Group, *Lancet* (1994) 343:311-22). Hence, an adjunctive anti-coagulant therapy that does not increase the risk of bleeding, but inhibits the formation of new thrombin, would be greatly beneficial.

It has been found that treatment of wild-type mice with an irreversible inhibitor of FXII led to fewer occluded vessels and less ischemic cortical damage, and inhibition of FXII would be protective for arterial thrombosis, such as that occurring during acute MI or during thrombotic stroke (WO2006/066878). However, peptidic drugs have numerous shortcomings, including limited application to acute studies due to short half-lives, i.v. administration requiring medical intervention, and the development of anti-peptide antibodies by patients undergoing treatment.

Plasma kallikrein has also been implicated in diabetic macular edema and retinopathy (A. Clermont et al., *Diabetes* (2011) 60:1590-98; J. A. Phipps et al., *Hypertension* (2009) 53:175-81); hereditary angioedema with C1 inhibitor deficiency (A. Banerji et al., *N Engl J* Med (2017) 376:717-28; E. Aygören-Pürsün et al., *N Engl J Med* (2018) 379(4):352-62); acute liver injury (M. Li et al., *Biochem Biophys Res Commun* (2018) 504(4):857-64); inflammation and anaphylaxis (L. Bender et al., *Front Immunol* (2017) 8:1115); exacerbation of hemorrhagic transformation and cerebral edema after treatment with recombinant tPA (F. Simão et al., *Blood* (2017) 129(16):2280-90); and chemical-sensitized renal damage (H. Wang et al., *J Immunotoxicol* (2016) 13(4):567-79).

The polymorphic behavior of drugs can be critical in pharmacology. Polymorphs are different solid forms of the same molecule, and can have different physical properties as a result of the arrangement of molecules in the crystal lattice.

These different properties can affect pharmaceutical parameters such as storage stability, compressibility, density, hygroscopy, dissolution rates, and bio-availability. It is often possible to convert one polymorph into another polymorph, and in some cases this happens spontaneously. Storage stability is affected when one polymorph can convert into a different polymorph having a different density or hygroscopy (which can cause tablets to swell or crumble). One polymorphic form of a compound may be more soluble or dissolve at a higher rate, increasing its bioavailability as compared to another polymorph. If a polymorph converts into a less bioavailable form, the potency of the dosage form can be reduced: if into a more bioavailable form, the drug may exceed its toxic limit. In addition, the physical properties of the form may affect manufacturing: for example, one polymorph might be more likely to form solvates or might be difficult to filter and wash free of impurities.

Suitable plasma kallikrein inhibitors have been developed (see, e.g., Sinha et al., WO2008/016883; U.S. Pat. No. 8,258,170). However, identification of crystalline forms for such compounds, and their suitability for formulation in solid forms, has not yet been reported. As different crystalline forms can differ in solubility, density, stability, and bioavailability, identification of such forms remains an unmet need.

BRIEF SUMMARY OF THE INVENTION

Provided herein are pure crystalline forms of 1-benzyl-N-(4-carbamimidoylbenzyl)-1H-pyrazole-4-carboxamide acetate, an amorphous form, and methods for making each form.

One aspect of the invention is a crystalline form of 1-benzyl-N-(4-carbamimidoyl-benzyl)-1H-pyrazole-4-carboxamide acetate ("Compound 1"), which can be Form I, Form II, Form III, or Form IV, wherein the crystalline form is substantially free of any other polymorphic form.

Another aspect of the invention is an amorphous form of Compound 1 ("Form V"), wherein the amorphous form is substantially free of any crystalline form.

Another aspect of the invention is a pharmaceutical composition comprising a therapeutically effective amount of a pure solid form (Form I, Form II, Form III, Form IV, or Form V) of Compound 1, together with a pharmaceutically acceptable carrier.

Another aspect of the invention is a method for making Form I, substantially free of any other crystalline form.

Another aspect of the invention is a method for making Form II, substantially free of any other crystalline form.

Another aspect of the invention is a method for making Form III, substantially free of any other crystalline form.

Another aspect of the invention is a method for making Form IV, substantially free of any other crystalline form.

Another aspect of the invention is a method for making Form V, substantially free of any crystalline form.

Another aspect of the invention is a method for treating a disorder mediated by plasma kallikrein, by administering a pharmaceutical composition of the invention.

DETAILED DESCRIPTION OF THE INVENTION

Definitions

Unless otherwise stated the following terms used in the specification and claims have the meanings given below.

The term "alkyl", by itself or as part of another substituent, means, unless otherwise stated, a straight or branched chain hydrocarbon radical, having the number of carbon atoms designated (i.e., $C_1$-$C_8$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms.

The term "composition" as used herein is intended to encompass a product comprising the specified ingredients in the specified amounts, as well as any product which results, directly or indirectly, from combination of the specified ingredients in the specified amounts.

The term "polymorphic form" refers to a crystalline or amorphous solid form of a compound. Polymorphic forms differ from each other in the orientation or arrangement of molecules within the crystal structure. The differences in arrangement lead to different intermolecular forces, which can produce differences in melting point, solubility, hardness, stability, bioavailability, chemical reactivity, and the like. Polymorphic forms of the same compound can be distinguished by those properties, and by their X-ray diffraction pattern. We have now prepared four crystalline polymorphic forms of Compound 1, and an amorphous form.

The term "amorphous" refers to a solid form having at most limited crystallinity as determined by XRPD. In an amorphous solid, the atoms are present in an unordered structure. In a crystalline substance, or in crystalline zones, the atoms have both a short-range order and a long-range order. Amorphous material, in contrast, only has a short-range order. The degree of crystallization of the active substance can be determined for example with the aid of dynamic differential calorimetry or x-ray diffractometry, including XRPD.

The term "solid form" means any crystalline or amorphous form of 1-benzyl-N-(4-carbamimidoylbenzyl)-1H-pyrazole-4-carboxamide acetate, and mixtures thereof.

The terms "Compound of Formula I" and "Compound 1" refer to 1-benzyl-N-(4-carbamimidoylbenzyl)-1H-pyrazole-4-carboxamide acetate salt.

Figure 1:
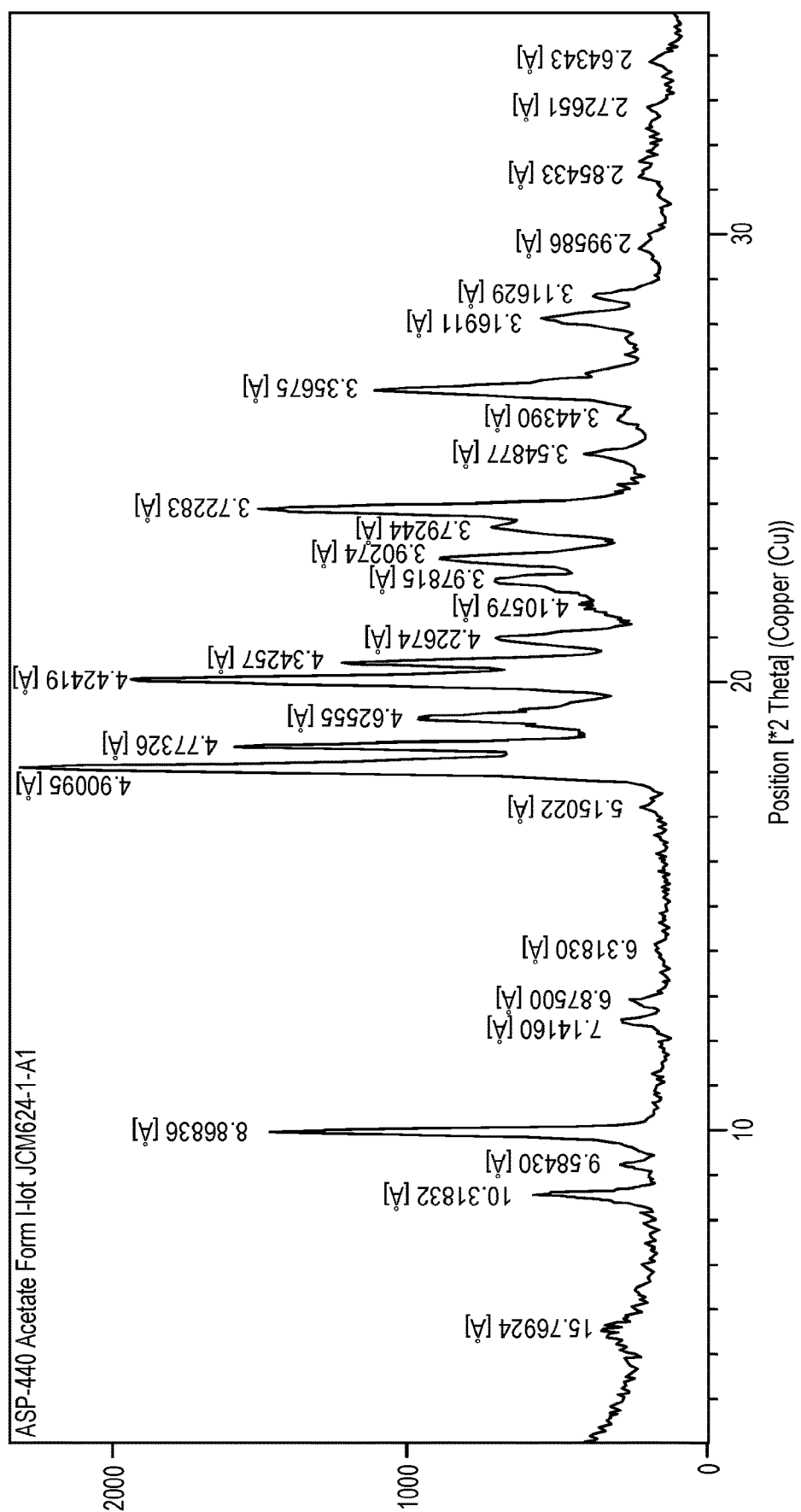
FIG. 1 depicts a powder X-ray diffraction (XRPD) pattern of crystalline Form I of Compound 1, made using Cu Kα radiation.

The term "Form I" as used herein refers to a pure anhydrous crystalline form of Compound 1. An XRPD diffraction pattern contains the following characteristic peaks: 10.0, 18.1, 18.6, 20.1, and 23.9 degrees, ±0.5, ±0.2, or ±0.1 degrees, 2θ, wherein said XRPD is made using Cu Kα radiation. A full diffraction pattern for Form I is set forth in FIG. 1. A "pure" crystalline form is substantially free of any other crystalline form.

The term "Form II" as used herein refers to a pure hydrated crystalline form of Compound 1. An XRPD diffraction pattern contains the following characteristic peaks: 4.2, 5.6, 8.4, 17.8, and 19.8 degrees, ±0.5, ±0.2, or ±0.1 degrees, 2θ, wherein said XRPD is made using Cu Kα radiation. A full diffraction pattern for Form II is set forth in FIG. 2.

Figure 3:
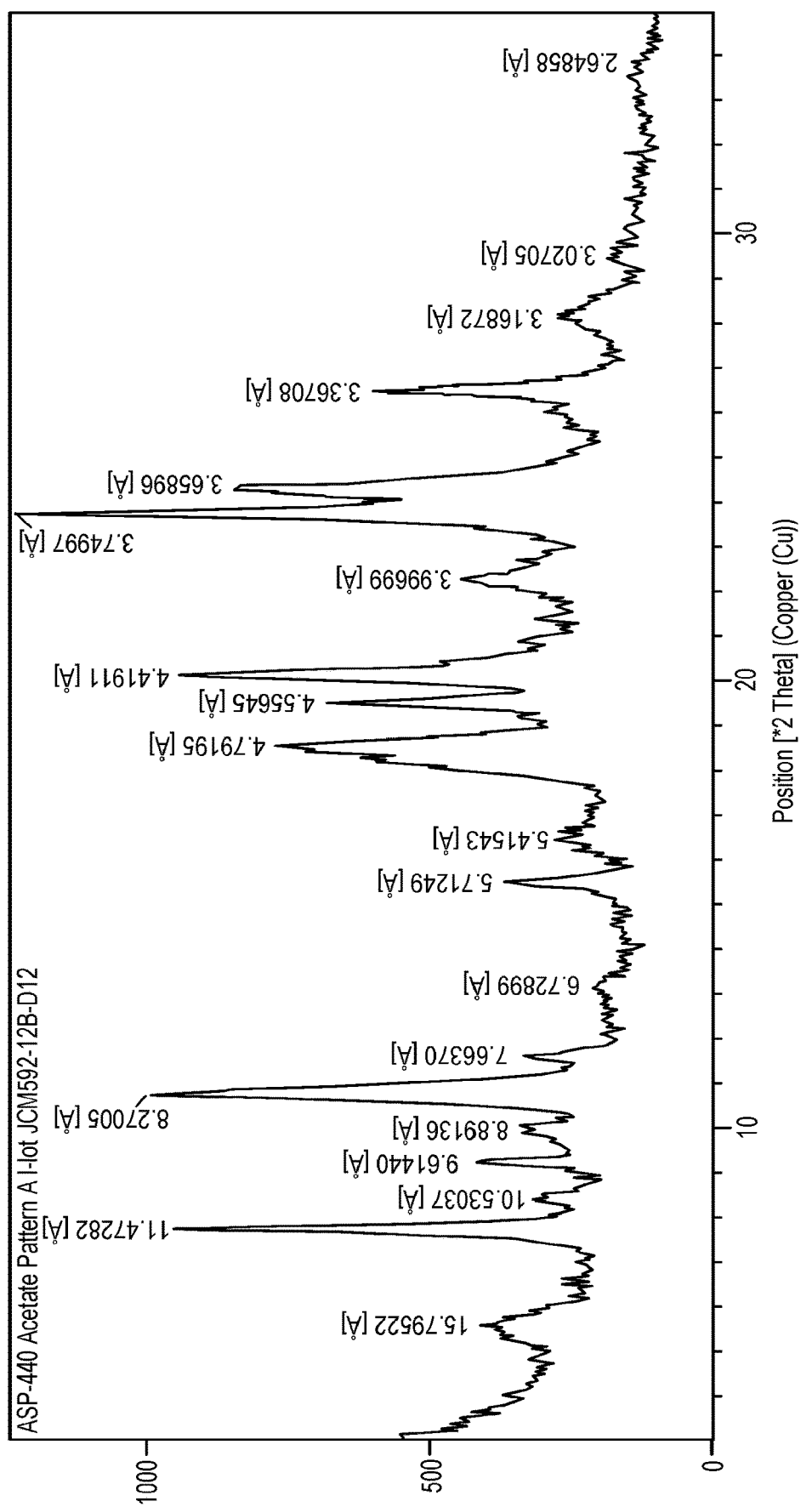
FIG. 3 depicts a powder X-ray diffraction (XRPD) pattern of crystalline Form III of Compound 1, made using Cu Kα radiation.

The term "Form III" as used herein refers to another pure crystalline form of Compound 1. An XRPD diffraction pattern contains the following characteristic peaks: 7.7, 10.7, 20.1, 23.7, and 24.3 degrees, ±0.5, ±0.2, or ±0.1 degrees, 2θ, wherein said XRPD is made using Cu Kα radiation. A full diffraction pattern for Form III is set forth in FIG. 3.

Figure 4:
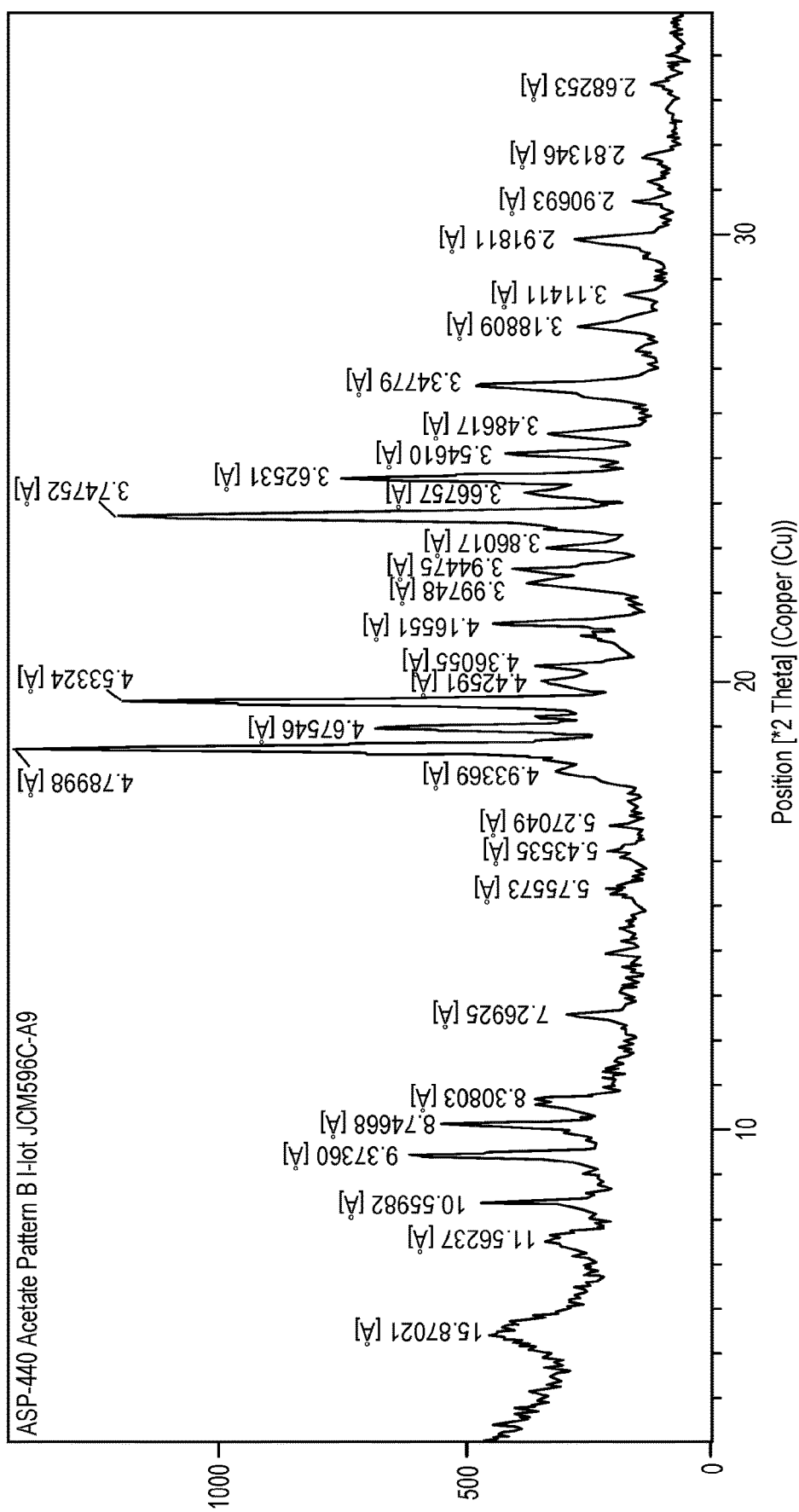
FIG. 4 depicts a powder X-ray diffraction (XRPD) pattern of crystalline Form IV of Compound 1, made using Cu Kα radiation.

The term "Form IV" as used herein refers to another pure crystalline form of Compound 1 An XRPD diffraction pattern contains the following characteristic peaks: 18.5, 19.6, and 23.7 degrees, ±0.5, ±0.2, or ±0.1 degrees, 2θ, wherein said XRPD is made using Cu Kα radiation. A full diffraction pattern for Form IV is set forth in FIG. 4.

The term "Form V" as used herein refers to a pure amorphous form of Compound 1. An XRPD diffraction pattern contains few or no characteristic peaks. A full diffraction pattern for Form V is set forth in FIG. 5.

The term "substantially free" as used herein refers to a solid form of Compound 1 that has at most a limited amount of a different polymorph. In some embodiments, a solid form of Compound 1 is substantially free of other polymorphic forms if it contains less than 10, 9, 8, 7, 6, 5, 4, 3, 2, 1, 0.9, 0.8, 0.7, 0.6, 0.5, 0.4, 0.3, 0.2, 0.1, 0.05, or 0.01% by weight of other polymorphic forms. For example, Form I is substantially free of other polymorphic forms if it consists of less than about 10%, less than about 5%, or less than about 1% by weight of Form II, Form III, Form IV, and/or Form V. The purity of such forms can be determined using XRPD, differential scanning calorimetry, thermos-gravimetric analysis, and other methods known in the art.

The term "subject" as used herein includes animals, such as mammals, including without limitation, primates (including humans), cows, pigs, sheep, goats, horses, dogs, cats, rabbits, rats, mice and the like.

The term "effective amount" refers to an amount that provides a therapeutic benefit in the treatment, prevention, or management of pathological processes mediated by plasma kallikrein or an overt symptom of pathological processes mediated by plasma kallikrein. The specific amount that is effective can be readily determined by an ordinary medical practitioner, and may vary depending on factors known in the art, such as, for example, the type of pathological processes, the patient's history and age, the stage of pathological processes, and the like. Inhibition of plasma kallikrein can be measured using known assays, for example without limitation, using a colorimetric or fluorometric substrate cleavage assay in vitro, or by measuring clotting time in whole blood or plasma ex vivo (see, e.g., U.S. Pat. No. 8,258,170).

General

Compound 1 is useful as a plasma kallikrein (PK) inhibitor, for the prevention and treatment of plasma kallikrein-dependent diseases or conditions, including disorders of blood coagulation, such as thrombosis, and other PK-dependent diseases and conditions. For example, the compounds inhibit the formation of thrombin by the intrinsic pathway and thus reduce the risk of new pathogenic thrombus formation (reocclusion), and also improve fibrinolytic-induced reperfusion when given as adjunctive therapy with a fibrinolytic regimen. Compound 1 is also useful for treating other disease and disorders that are mediated by plasma kallikrein, for example, without limitation, diabetic macular edema, diabetic retinopathy, hereditary angioedema with C1 inhibitor deficiency, acute liver injury, inflammation and anaphylaxis, exacerbation of hemorrhagic transformation and cerebral edema after treatment with recombinant tissue plasminogen activator (tPA), chemical-sensitized renal damage, ischemic stroke, hemorrhagic stroke, hypertension and its vascular complications (including retinopathy and nephropathy), cerebrovascular edema, pulmonary hypertension, inflammation, pain, acute myocardial infarction (MI), deep vein thrombosis (DVT), complications from fibrinolytic treatment (e.g., with tissue plasminogen activator, streptokinase) following stroke or MI, angina, angioedema, sepsis, arthritis, complications of cardiopulmonary bypass, capillary leak syndrome, inflammatory bowel disease, diabetes and its vascular complications (including retinopathy, diabetic macular edema, nephropathy and neuropathy), age-related macular degeneration, retinal vein occlusions, brain edema, ischemia-reperfusion injury, angiogenesis (e.g., in cancer), asthma, anaphylaxis, and cerebrovascular complications of neurological conditions (e.g., Alzheimer's Disease, Parkinson's Disease, multiple sclerosis, CNS infections, and glioblastoma multiforme).

Plasma kallikrein (PK), a serine protease present in plasma as the inactive zymogen precursor plasma prekallikrein (prePK), is proteolytically activated by FXIIa. In a positive feedback loop, PK proteolytically activates the zymogen FXII, leading to additional FXIIa formation, further amplifying its own activation. FXIIa also activates the zymogen FXI to active FXIa, which results in the initiation of the intrinsic (contact) pathway of blood coagulation, resulting in generation of thrombin, and cleavage of fibrinogen. Importantly, PK cleaves high molecular weight kininogen (HMWK) to generate bradykinin. Bradykinin is able to open the tight junctions between endothelial cells lining blood vessels by activating its receptors, B1 and B2, present on the endothelial cells' surface, and thus allowing fluid and plasma protein to extravasate into tissue, a condition known as increased vascular permeability. Disruption of tight junctions of the blood-brain barrier, and consequent leakage of plasma and proteins into the brain (edema) have also been associated with neurodegenerative diseases, such as Alzheimer's Disease, Parkinson's Disease, and multiple sclerosis (MS), as well as with CNS infections and brain tumors. For example, peritumoral brain edema results in poorer prognosis in patients with glioblastoma multiforme (K. Schoenegger et al., *Eur J Neurol.* (2009) 16(7):874-78). The increased vascular permeability caused by bradykinin formation can result in the accumulation of excess fluid (edema) in many tissues and organs in various diseases, e.g., angioedema, cystoid macular edema, diabetic macular edema, macular edema after retinal vein occlusion, cerebrovascular edema following stroke or head trauma, and capillary leak syndrome. For example, Compound 1 has been shown to reduce retinal vascular permeability in angiotensin-II-treated rodents, as did the BK receptor antagonist Hoe-140 (J. A. Phipps et al., *Hypertension* (2009) 53:175-81). Activation of prePK and the contact system has also been shown to cause anaphylaxis, e.g., in patients treated with contaminated heparin (T. K. Kishimoto et al., *N. Engl. J. Med.* (2008) 358:2457-67).

The importance of BK in vasogenic edema is further illustrated in hereditary angioedema, in which individuals have little or no functional C1-Inhibitor (the major endogenous inhibitor of PK). High levels of bradykinin are generated in these individuals resulting in extravasation of fluid and protein from the plasma into soft tissue, thus causing life-threatening edema. C1-Inhibitor is also known to be involved in the pathogenesis of age-related macular degeneration (S. Ennis et al., *Lancet* (2008) 372:1828-34) and ischemia-reperfusion injury following organ transplant or myocardial infarction (D. Inderbitzin et al., *Eur. Surg. Res.* (2004) 36:142-47; G. Horstick et al., *Circulation* (2001) 104:3125-31). Bradykinin and its receptors have been shown to be involved in tumor angiogenesis (Y. Ikeda et al. *Cancer Res* (2004) 64:5178-85), pulmonary hypertension (L. Taraseviciene-Stewart et al. *Peptides* (2005) 26:1292-300), and asthma (P. J. Barnes, "Recent Progress on Kinins", (1992) AAS38/III, Birkhauser Verlag, Basel).

In patients with angioedema conditions, a small polypeptide PK inhibitor (DX-88, ecallantide) alleviates edema in patients with hereditary angioedema (A. Williams et al., *Transfus. Apher. Sci.* (2003) 29:255-58; L. Schneider et al., *J Allergy Clin Immunol.* (2007) 120(2):416-22; J. H. Levy et al., *Expert Opin. Invest. Drugs* (2006) 15:1077-90). A bradykinin B2 receptor antagonist, icatibant, is also effective in treating hereditary angioedema (K. Bork et al., *J. Allergy Clin. Immunol.* (2007) 119:1497-503). PK generates bradykinin, therefore inhibition of PK inhibits bradykinin production.

In thrombogenesis resulting from fibrinolytic treatment (e.g., tissue plasminogen activator, streptokinase), higher levels of PK are found in patients undergoing fibrinolysis (H. M. Hoffmeister et al., *J Cardiovasc. Pharmacol.* (1998) 31:764-72). Plasmin-mediated activation of the intrinsic pathway has been shown to occur in plasma and blood, and was markedly attenuated in plasma from individuals deficient in any of the intrinsic pathway components (G. A. Ewald et al., *Circulation* (1995) 91:28-36). Individuals who have had an acute MI were found to have elevated levels of activated PK and thrombin (H. M. Hoffmeister et al., *Circulation* (1998) 98:2527-33).

Ecallantide reduced brain edema, infarct volume and neurological deficits in an animal model of ischemic stroke (C. Storini et al., *J Pharm. Exp. Ther.* (2006) 318:849-54). C1-INH reduced infarct size in a mouse model of middle cerebral artery occlusion (M. G. De Simoni et al., *Am. J. Pathol.* (2004) 164:1857-63; N. Akita et al., *Neurosurg.* (2003) 52:395-400). Compound 1 was shown to reduce infarction volume and cerebrovascular edema in a rat model of ischemic stroke, and expansion of intracerebral hemorrhage in a model of hemorrhagic stroke (WO2009/0971). B2 receptor antagonists were found to reduce the infarct volume, brain swelling, and neutrophil accumulation, and were neuroprotective in an animal model of ischemic stroke (S. Zausinger et al., *Acta Neurochir. Suppl.* (2003) 86:205-07; D. B. Lumenta et al., *Brain Res.* (2006) 1069:227-34; L. Ding-Zhou et al., *Br. J. Pharmacol.* (2003) 139:1539-47).

It has been found that prePK levels are higher in diabetics, especially those with proliferative retinopathy, and correlate with fructosamine levels (B.-B. Gao et al., *Nature Med.* (2007) 13:181-88; K. Kedzierska et al., *Archives Med. Res.* (2005) 36:539-43). PrePK is also found to be elevated in diabetics and is highest in those with a sensomotor neuropathy (M. Christie et al., *Thromb. Haemostas.* (1984) 52:221-23). PrePK levels are elevated in diabetics, and are associated with increased blood pressure, independently correlate with the albumin excretion rate, and are elevated in diabetics with macroalbuminuria, suggesting prePK may be a marker for progressive nephropathy (A. A. Jaffa et al., *Diabetes* (2003) 52:1215-21). B1 receptor antagonists have been found to decrease enhanced vascular permeability and plasma leakage into various organs, including the skin and retina, in rats with streptozotocin-induced diabetes (S. R. Lawson et al., *Eur. J. Pharmacol.* (2005) 514:69-78; S. R. Lawson et al., *Regul Pept.* (2005) 124:221-24). B1 receptor antagonists can also prevent streptozotocin-treated mice from developing hyperglycemia and renal dysfunction (A. Zuccollo et al., *Can. J. Physiol. Pharmacol.* (1996) 74:586-89).

One aspect of the invention is a crystalline form of 1-benzyl-N-(4-carbamimidoyl-benzyl)-1H-pyrazole-4-carboxamide acetate ("Compound 1"), substantially free of other polymorphic forms of 1-benzyl-N-(4-carbamimidoyl-benzyl)-1H-pyrazole-4-carboxamide acetate. An embodiment of the invention is the crystalline form having less than 10% by weight of any other polymorphic form. An embodiment of the invention is the crystalline form having less than 5% by weight of any other polymorphic form. An embodiment of the invention is the crystalline form having less than 1% by weight of any other polymorphic form.

Another aspect of the invention is an amorphous form of Compound 1, substantially free of other polymorphic forms of Compound 1.

Another aspect of the invention is a pharmaceutical composition comprising a pharmaceutically acceptable carrier, and a solid form of Compound 1 which is substantially free of any other solid form of Compound 1.

Another aspect of the invention is a method for making a solid form of Compound 1 which is substantially free of any other solid form of Compound 1.

Compound Preparation

Compounds of Formula I are made by the processes described herein:

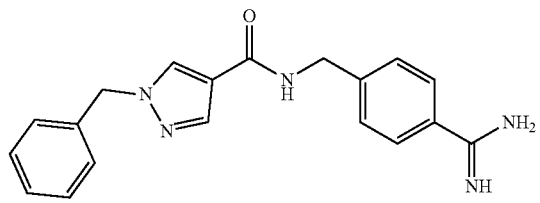

(Formula I)

The process of the invention has been optimized for yield and purity to a degree sufficient for commercialization. 1-Benzyl-1H-pyrazole-4-carboxylic acid ("Compound 4") can be obtained from commercial sources, or are prepared by methods known in the art from precursor compounds that are commercially available. For example, 1-benzyl-1H-pyrazole-4-carboxylic acid may be prepared from ethyl 1H-pyrazole-4-carboxylate by contacting it with a suitably substituted benzyl halide (for example benzyl bromide) in an aprotic solvent in the presence of a strong base, followed by hydrolysis of the ester. For example, ethyl 1H-pyrazole-3-carboxylate is treated with $K_2CO_3$ in acetone, followed by benzyl bromide to produce the compound ethyl 1-benzyl-1H-pyrazole-3-carboxylate. The ethyl ester is then treated with, for example, KOH in methanol to provide the free acid (Compound 4).

A. Process Step 1:

(A) Compound 4 can be coupled with 4-aminomethyl-benzonitrile using 1-propane-phosphonic acid cyclic anhydride (T3P®) and triethylamine ($Et_3N$) in an aprotic solvent to produce 1-benzyl-N-(4-cyanobenzyl)-1H-pyrazole-4-carboxamide ("Compound 3").

In one group of embodiments of the process, the T3P® is provided as a 50% solution in ethyl acetate. Compound 4 and the 4-aminomethyl-benzonitrile can be provided in about equimolar amounts, or one of the reactants can be provided in an excess ranging from about 0.2 to about 5 equivalents compared to the other reactant. In an embodiment of the process, the ratio of Compound 4 to 4-aminomethylbenzonitrile is from about 0.2 to about 5, from about 0.5 to about 2, from about 0.9 to about 1.2, or about 1.0. The T3P® can be provided in a range of ratios as well. In embodiments of the process, the ratio of T3P® to Compound 4 can be from about 0.5 to about 5, from about 0.8 to about 4, from about 1.0 to about 3, from about 1.2 to about 2.0, and from about 1.2 to about 1.8. The triethylamine can also be provided in a range of ratios to Compound 4. In embodiments of the process, the ratio of $Et_3N$ to Compound 4 is from about 0.5 to about 10, from about 1 to about 8, from about 2 to about 5, and from about 3 to about 5.

In some embodiments of the process, an aprotic solvent is used, for example without limitation, dichloromethane (DCM), tetrahydrofuran (THF), methyl ethyl ketone (MEK), dimethylsulfoxide (DMSO), ethyl acetate (EtOAc), methyl t-butyl ether (MTBE), and mixtures thereof. In one embodiment of the process, the aprotic solvent is DCM.

The coupling of Compound 4 and 4-(aminomethyl)benzonitrile is typically conducted at a temperature range of from about 0° C. to about 100° C. In some embodiments, the coupling reaction temperature is from about 15° C. to about the reflux temperature of the selected aprotic solvent. In embodiments of the process, the reaction temperature is from about 20° C. to about 80° C. In some embodiments of the process, the reaction temperature is from about 20° C. to about 30° C.

The coupling reaction noted above is typically run for a suitable length of time for the reaction to go substantially to completion, which may vary with the aprotic solvent, and reaction temperature selected. In some embodiments of the process, the reaction time is about 30 minutes to about 48 hours. In some embodiments of the process, the reaction time is about 1 hour to about 24 hours. In other embodiments of the process, the reaction time is about 4 hours to about 12 hours. In still other embodiments of the process, the reaction time is about 6 hours to about 10 hours. In some embodiments of the process, the reaction time is about 8 hours.

In some embodiments of the process, the reaction is conducted under an inert atmosphere or anhydrous conditions. In some embodiments of the process, the reaction is conducted under nitrogen.

(B) The product of the above coupling reaction, Compound 3, is then purified by extraction. In general, (i) the aprotic solvent containing Compound 3 is combined with water, (ii) mixed well (e.g., by stirring or shaking), (iii) the organic and aqueous layers allowed to separate, (iv) the aqueous layer is removed, and (v) the organic layer is dried to remove water. These steps, together or individually, may be repeated one, two, or three or more times. Further, the water may also contain salts, such as NaCl, $NaHCO_3$, and the like. The aqueous layers may also be extracted with an organic solvent, for example with DCM, and that organic solvent can be combined with the other organic layers obtained. The organic layer may then be dried over a suitable drying agent, such as sodium sulfate.

In some embodiments of the process, Compound 3 in DCM is stirred with water, and the layers separated, then stirred with 10% aqueous $NaHCO_3$, separated, then saturated aqueous NaCl, and separated, followed by drying over $Na_2SO_4$.

In some embodiments of the process, the dried organic layer is then concentrated under reduced pressure, and taken up in acetone, washed with water, filtered, suction dried, and vacuum dried (or dried under reduced pressure) to provide purified Compound 3. The drying steps may be performed at elevated temperatures, for example above about 25° C., above about 30° C., above about 35° C., above about 40° C., above about 45° C., above about 50, above about 55° C., and above about 60° C. The drying temperature is generally lower than the melting temperature of Compound 3, and can be lower than about 150° C., lower than about 120° C., lower than about 100° C., lower than about 90° C., lower than about 80° C., lower than about 75° C., lower than about 70° C., and lower than about 65° C.

B. Process Step 2:

(A) Compound 3 is then contacted with hydroxyl amine ($NH_2OH$) or a salt thereof in the presence of a weak base, in a suitable solvent, to provide a Compound 2 solution. In embodiments of the process, the hydroxylamine is hydroxylamine hydrochloride. The hydroxylamine or hydroxylamine salt is added to the reaction in a ratio to Compound 3 of about 10 to about 0.5. In some embodiments of the process, the ratio of $NH_2OH$ or salt to Compound 3 is about 10, about 9, about 8, about 7, about 6, about 5, about 4, about 3, about 2, or about 1. In some embodiments of the process, the ratio is at least about 0.5, about 1, about 2, or about 3.

In some embodiments of the process, the weak base used in the conversion of Compound 3 to Compound 2 is triethylamine or diisopropylamine. The weak base is generally added to the reaction mixture in a ratio to Compound 3 of about 10 to about 0.5. In some embodiments of the process, the ratio of weak base to Compound 3 is about 10, about 9, about 8, about 7, about 6, about 5, about 4, about 3, about 2, or about 1. In some embodiments of the process, the ratio is at least about 0.5, about 1, about 2, or about 3.

In some embodiments of the process (the conversion of Compound 3 to Compound 2), the solvent is ethanol, isopropanol, methanol, DCM, EtOAc, or mixtures thereof.

In some embodiments of the conversion process of Compound 3 to Compound 2, the reaction is carried out at elevated temperature, for example above about 25° C., above about 30° C., above about 35° C., above about 40° C., above about 45° C., above about 50, above about 55° C., above about 60° C., above about 65° C., and above about 70°

C. The reaction temperature is generally at or lower than the reflux temperature of the selected solvent, and can be lower than about 120° C., lower than about 100° C., lower than about 90° C., lower than about 80° C., lower than about 75° C., lower than about 70° C., and lower than about 65° C.

In some embodiments of the conversion process of Compound 3 to Compound 2, the reaction time is in general the length of time required for the reaction to go substantially to completion, which may vary with the particular reactants, aprotic solvent, and reaction temperature selected. In some embodiments of the process, the reaction time is about 30 minutes to about 48 hours. In embodiments of the process, the reaction time is about 1 hour to about 24 hours. In embodiments of the process, the reaction time is about 4 hours to about 12 hours. In embodiments of the process, the reaction time is about 6 hours to about 10 hours. In some embodiments of the process, the reaction time is about 7 hours.

(B) The Compound 2 solution is then (i) concentrated, (ii) the compound precipitated by adding water, (iii) the solids are filtered, (iv) washed, and (v) dried to provide a purified Compound 2. In some embodiments of the process, (i) concentration is effected by heating the solution containing the Compound 2, by reducing the pressure, or both. In some embodiments of the process, the solution is concentrated by heating under reduced pressure to a volume of about 20% of the volume of the reaction mixture. In some embodiments of the process, the solids are dried by suction filtration, drying under reduced pressure, drying at elevated temperature, or a combination thereof. In some embodiments of the process, the solids are first dried by suction filtration, then by drying at elevated temperature under reduced pressure to provide purified Compound 2.

C. Process Step 3:

(A) Compound 2 is then subjected to reducing conditions in a protic solvent at an elevated temperature to provide a crude Compound 1. In some embodiments of the process, the reducing conditions comprise catalytic hydrogenation. In some embodiments of the process, the catalytic hydrogenation uses Raney nickel and hydrogen. In some embodiments of the process, the protic solvent is acetic acid. This process can, in some embodiments, provide Compound 1 as an acetate salt.

In some embodiments of the conversion of Compound 2 to Compound 1 process, an elevated reaction temperature is used that is above about 30° C., above about 35° C., above about 40° C., above about 45° C., above about 50, above about 55° C., or above about 60° C. The reaction temperature is generally at or lower than the reflux temperature of the solvent, and is lower than about 120° C., lower than about 100° C., lower than about 90° C., lower than about 80° C., lower than about 75° C., lower than about 70° C., lower than about 65° C., lower than about 60° C., or lower than about 55° C. In some embodiments of the process, the reaction temperature is about 50° C. to about 55° C.

In some embodiments of the conversion of Compound 2 to Compound 1 process, the catalytic hydrogenation employs a metal catalyst. In some embodiments, the metal catalyst comprises nickel. In other embodiments, the metal catalyst comprises Raney nickel.

The amount of catalyst used in the reduction of Compound 2 to Compound 1 can vary depending on the catalyst and other reaction conditions selected. In some embodiments of the process, the amount of Raney nickel used is (expressed as a mol % based on the amount of Compound 2) at least about 1 mol %, at least about 5 mol %, at least about 10 mol %, at least about 15 mol %, at least about 20 mol %, at least about 25 mol %, at least about 30 mol %, at least about 35 mol %, at least about 40 mol %, at least about 45 mol %, at least about 50 mol %, or at least about 60 mol %.

Similarly, the amount of hydrogen used (expressed as kg pressure per $cm^3$ of catalyst) will also vary depending on the amount of catalyst and other reaction conditions selected. In some embodiments of the process, the amount of hydrogen is at least about 1 $kg/cm^3$, at least about 2 $kg/cm^3$, at least about 3 $kg/cm^3$, at least about 4 $kg/cm^3$, at least about 5 $kg/cm^3$, at least about 6 $kg/cm^3$, at least about 7 $kg/cm^3$, at least about 8 $kg/cm^3$, at least about 9 $kg/cm^3$, at least about 10 $kg/cm^3$, at least about 11 $kg/cm^3$, at least about 12 $kg/cm^3$, at least about 15 $kg/cm^3$, at least about 20 $kg/cm^3$, or at least about 25 $kg/cm^3$. In some embodiments, the reaction employs about 20 mol % Raney nickel and about 10 $kg/cm^3$ $H_2$.

The reaction time is in general the length of time required for the reduction to go substantially to completion, which may vary with the particular conditions and reaction temperature selected. In some embodiments, the reaction time is at least about 30 minutes, at least about 1 hour, at least about 4 hours, at least about 8 hours, at least about 10 hours, at least about 12 hours, at least about 16 hours, at least about 20 hours, or at least about 24 hours. In other embodiments, the reaction time is less than about 48 hours, less than about 40 hours, less than about 36 hours, less than about 30 hours, less than about 24 hours, less than about 18 hours, or less than about 14 hours. In some embodiments, the reaction time is about 12 hours.

(B) The crude Compound 1 reaction mixture is (i) filtered, (ii) the residue washed with a first solvent, then (iii) concentrated to about 10-20% of the reaction mixture volume, and (iv) the reaction mixture subjected to a second solvent in which the compound is less soluble, (v) filtered and (vi) dried to provide a semi-purified product. The first solvent (step ii) may be a lower alkyl alcohol, dimethylsulfoxide (DMSO), or dimethylformamide (DMF). In some embodiments, the first solvent is methanol or ethanol. In some embodiments of the process, the second solvent (step iv) is ethyl acetate.

The filtering process (steps i and v) may comprise suction filtering, and further comprise washing the solid with additional second solvent. In embodiments of the process, the drying process (step vi) may include suction drying, drying under reduced pressure, drying at an elevated temperature, or a combination thereof. In other embodiments of the process, the drying process includes suction drying, followed by drying under reduced pressure at a temperature of at least 35° C. In some embodiments, the reduced pressure is less than 600 mmHg, less than 500 mmHg, less than 400 mmHg, less than 300 mmHg, or less than 200 mmHg. In some embodiments, the drying temperature is at least about 40° C., at least about 45° C., or at least about 50° C. One of skill in the art will appreciate that the drying temperature is less than either the melting point of, or decomposition temperature of Compound 1. In some embodiments, the drying temperature is less than about 120° C., less than about 110° C., less than about 100° C., less than about 90° C., less than about 80° C., less than about 70° C., or less than about 65° C.

(C) The semi-purified product (Compound 1) at this point may still contain an unacceptable amount of nickel (or other catalyst metal). To further purify the product, the dried solid is (i) subjected to water, (ii) heated at an elevated temperature and stirred to form a slurry, (iii) cooled and (iv) filtered, (v) dried a first time, (vi) taken up in a mixture of ethanol and acetic acid, (vii) heated to a holding temperature, (viii) cooled, (ix) filtered, and (x) dried a second time to provide a nickel-depleted product. In some embodiments of the process, the elevated temperature of step (ii) is at least about 30° C., at least about 35° C., at least about 40° C., at least about 45° C., at least about 50° C., at least about 55° C., at least about 60° C., or at least about 65° C. In some embodiments of the process, the elevated temperature is less than about 100° C., less than about 90° C., less than about 80° C., less than about 70° C., or less than about 65° C. In some embodiments of the process, the elevated temperature is about 55° C. In some embodiments of the process, the filtering process of step (iv) includes suction filtering and washing with water. In some embodiments of the process, the drying step of step (v) includes suction drying followed by drying under reduced pressure at a temperature of at least 35° C. In some embodiments of the process, the reduced pressure is less than 600 mmHg, less than 500 mmHg, less than 400 mmHg, less than 300 mmHg, or less than 200 mmHg. In some embodiments of the process, the drying temperature of step (v) is at least about 40° C., at least about 45° C., or at least about 50° C. In embodiments of the process, the drying temperature is less than about 120° C., less than about 110° C., less than about 100° C., less than about 90° C., less than about 80° C., less than about 70° C., or less than about 65° C. In some embodiments of the process, the drying temperature of step (v) is about 45° C.

In step (vi), the ratio of ethanol to acetic acid may range from about 1:20 to about 20:1. In some embodiments of the process, the ratio is about 1:1, about 2:1, about 3:1, about 4:1, about 5:1, about 6:1, about 7:1, about 8:1, about 9:1, or about 10:1, v/v ethanol:acetic acid.

In some embodiments of the process, the holding temperature of step (vii) is at least about 30° C., at least about 35° C., at least about 40° C., at least about 45° C., at least about 50° C., at least about 55° C., at least about 60° C., or at least about 65° C. In some embodiments of the process, the holding temperature is about the reflux temperature of the solvent mixture of ethanol and acetic acid, or less than about 80° C., less than about 75° C., less than about 70° C., less than about 65° C., or less than about 60° C. In some embodiments of the process, the holding temperature is about the reflux temperature of the solvent mixture.

In some embodiments of the process, the mixture is maintained at the holding temperature for a time period of at least about 10 minutes, at least about 20 minutes, at least about 30 minutes, at least about 45 minutes, at least about 60 minutes, at least about 90 minutes, at least about 120 minutes, at least about 150 minutes, at least about 240 minutes, or at least about 3 hours. In some embodiments of the process, the time period is no more than about 5 hours, no more than about 4 hours, no more than about 3 hours, no more than about 2 hours, no more than about 1 hour, or no more than about 30 minutes. In some embodiments of the process, the time period is about 1 hour.

The cooling described for step (viii) is generally performed over a time period of at least about 10 minutes, at least about 20 minutes, at least about 30 minutes, at least about 45 minutes, at least about 1 hour, or at least about 2 hours. The final temperature of step viii is less than about 35° C., less than about 30° C., less than about 25° C., less than about 20° C., less than about 15° C., less than about 10° C., or less than about 5° C. In some embodiments of the process, the final temperature of step (viii) is about ambient temperature. In some embodiments, step (viii) further comprises stirring the mixture.

The filtering of step (ix) may further include washing with a lower alkyl alcohol. In some embodiments, the filtered solids are washed with ethanol. The drying step of step (x) may include suction drying, drying under reduced pressure, drying at an elevated temperature, or a combination thereof. In embodiments of the process, the drying process of step (x) includes suction drying followed by drying under reduced pressure at a temperature of at least 35° C. In embodiments of the process, the reduced pressure is less than 600 mmHg, less than 500 mmHg, less than 400 mmHg, less than 300 mmHg, or less than 200 mmHg. In some embodiments of the process, the drying temperature of step (x) is at least about 40° C., at least about 45° C., or at least about 50° C. As noted above, the drying temperature used will be less than the melting point of Compound 1, and less than the decomposition temperature of Compound 1. In some embodiments of the process, the drying temperature is less than about 120° C., less than about 110° C., less than about 100° C., less than about 90° C., less than about 80° C., less than about 70° C., or less than about 65° C. In some embodiments of the process, the drying temperature of step (x) is about 45° C. In some embodiments of the process, steps (vi)-(x) are repeated 1, 2, or 3 times. In embodiments of the process, steps (vi)-(x) are repeated once.

Crystalline Forms

An aspect of the invention is a crystalline form of 1-benzyl-N-(4-carbamimidoyl-benzyl)-1H-pyrazole-4-carboxamide acetate ("Compound 1"), substantially free of other polymorphic forms of 1-benzyl-N-(4-carbamimidoylbenzyl)-1H-pyrazole-4-carboxamide acetate. An embodiment of the invention is the form having less than 10% by weight of any other polymorphic form. An embodiment of the invention is the form having less than 5% by weight of any other polymorphic form. An embodiment of the invention is the form having less than 1% by weight of any other polymorphic form.

A. Form I:

(A) The nickel-depleted product of Process Step 3 above is further purified by (i) contacting the compound with a first solvent, (ii) raising the mixture to a first elevated temperature, (iii) adding a second solvent, (iv) cooling the resulting mixture to a crystallizing temperature, (v) stirring the mixture, (vi) filtering the solid, and (vii) drying the solid, to provide Compound 1 as pure anhydrous crystalline Form I.

In some embodiments, the first solvent of step (i) is methanol, ethanol, 1-propanol, or 2-propanol, or a mixture thereof. In some embodiments, the lower alkyl alcohol is methanol.

In some embodiments, the first elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the first solvent, or no more than about 80° C., no more than about 75° C., no more than about 70° C., no more than about 60° C., no more than about 55° C., no more than about 50° C., no more than about 45° C., no more than about 40° C., or no more than about 35° C. In some embodiments, the elevated temperature is about 55° C. In some embodiments, step (ii) further comprises maintaining the mixture at or near the elevated temperature until Compound 1 has completely dissolved, and a clear solution has formed. In some embodiments, step (ii) further includes slowly cooling the solution to a second elevated temperature. In some embodiments, the second elevated temperature is about 5° C., about 10° C., about 15° C., or about 20° C. lower than the first elevated temperature. The second elevated temperature is about 5° C., about 10° C., about 15° C., or about 20° C. above 20° C. In some embodiments, step (ii) also includes filtering the solution.

In some embodiments, the second solvent of step (iii) is MTBE or THF. In some embodiments, the second solvent is MTBE. In some embodiments, the first solvent and second solvent are anhydrous. In some embodiments, the second solvent is added slowly, over an extended time period, of at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, at least about 180 minutes, or at least about 240 minutes. The extended time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour. In some embodiments, the extended time period is about 2 hours. The ratio of the first solvent to the second solvent can vary from about 1:20 to about 20:1, v/v. In some embodiments, the ratio of MeOH to MTBE is about 5:1, about 4:1, about 3:1, about 2.7:1, about 2.5:1, about 2.3:1, about 2:1, about 1.5:1, about 1.3:1, about 1.2:1, about 1:1, about 1:1.5, about 1:2, about 1:3, or about 1:4.

In some embodiments, step (iii) further includes adding a seed crystal.

The crystallizing temperature of step (iv) is no more than about 35° C., less than about 30° C., less than about 25° C., less than about 20° C., less than about 15° C., less than about 10° C., or less than about 5° C. In some embodiments, the crystallizing temperature is about 25° C. One of skill in the art will appreciate that the cooling will generally occur over an extended time period. In some embodiments, the cooling time of step (iv) is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, or at least about 180 minutes. In some embodiments, the cooling time is about 45 minutes to about 90 minutes.

In some embodiments of the invention, step (v) further includes adding an additional amount of the second solvent over an extended period of time. In some embodiments, the extended time period of step (v) is at least about 20 minutes, at least about 30 minutes, at least about 45 minutes, at least about 60 minutes, at least about 75 minutes, at least about 90 minutes, at least about 105 minutes, at least about 120 minutes, or at least about 150 minutes. In other embodiments, the extended time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour.

The filtering step of step (vi) can further include washing the solid with an additional amount of the second solvent. The drying step of step (vii) may include suction drying, drying under reduced pressure, drying at an elevated temperature, or a combination thereof. In some embodiments, the drying invention of step (x) includes suction drying followed by drying under reduced pressure at a temperature of at least 35° C. In some embodiments, the reduced pressure is less than 600 mmHg, less than 500 mmHg, less than 400 mmHg, less than 300 mmHg, or less than 200 mmHg. In some embodiments, the drying temperature of step (vii) is at least about 40° C., at least about 45° C., or at least about 50° C. As noted above, the drying temperature is less than the melting point of Compound 1, and less than the decomposition temperature of Compound 1. In some embodiments, the drying temperature is less than about 120° C., less than about 110° C., less than about 100° C., less than about 90° C., less than about 80° C., less than about 70° C., or less than about 65° C. In some embodiments, the drying temperature of step vii is about 45° C.

An aspect of the invention is the crystalline form of Compound 1 which is anhydrous and characterized by having a melting point of about 253° C., and an aqueous solubility of about 8.3 mg/mL at 25° C. ("Form I"). An embodiment of the invention is the crystalline form of Compound 1 which has an XRPD pattern that comprises peaks at 10.0, 18.1, 18.6, 20.1, and 23.9 degrees, ±0.5, ±0.2, or ±0.1 degrees, 2θ, wherein said XRPD pattern is made using Cu Kα radiation. An embodiment of the invention is the crystalline form of Compound 1 wherein the XRPD pattern further comprises a peak at 20.5 degrees, ±0.5, ±0.2, or ±0.1 degrees, 2θ. An embodiment of the invention is the crystalline form of Compound 1 having an XRPD pattern which is substantially similar to the pattern of FIG. 1.

An aspect of the invention is the method of making Form I, by contacting a solid form of Compound 1 with a solvent selected from the group consisting of methanol, isopropanol, tetrahydrofuran, 2-methyl-tetrahydrofuran, anhydrous acetone, dichloromethane, diethyl ether, 3-methyl-1-butanol, and nitromethane, or a mixture thereof, for a period of time sufficient to produce Form I. An embodiment of the invention is the method wherein the solvent is methanol.

B. Form II:

Compound 1, in any solid form, is converted to Form II in the following process. Compound 1 is (i) contacted with an organic solvent and water mixture, (ii) heated and held for a first period of time, (iii) a second solvent is added, (iv) the mixture is cooled and held for a second period of time to crystallize, and (v) the resulting solid is isolated to provide Compound 1 as pure crystalline Form II. In some embodiments, the organic solvent of step (i) is methanol, isopropanol, THF, or acetone. In some embodiments, the organic solvent is methanol. In some embodiments, the organic solvent and water mixture comprises at least about 1% water, at least about 2% water, at least about 3% water, at least about 4% water, or at least about 5% water. In some embodiments, the organic solvent and water mixture comprises at least about 10% water, at least about 15% water, at least about 20% water, at least about 25% water, at least about 30% water, at least about 35% water, at least about 40% water, at least about 45% water, or at least about 50% water. In some embodiments, the organic solvent and water mixture comprises no more than about 45% water, no more than about 40% water, no more than about 35% water, no more than about 30% water, no more than about 25% water, no more than about 20% water, no more than about 15% water, or no more than about 10% water.

The elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the solvent mixture, or no more than about 80° C., no more than about 75° C., no more than about 70° C., no more than about 60° C., no more than about 55° C., no more than about 50° C., no more than about 45° C., no more than about 40° C., or no more than about 35° C. In some embodiments, the elevated temperature is about 55° C. In some embodiments, step (ii) further comprises maintaining the mixture at or near the elevated temperature until the Compound 1 has completely dissolved, and a clear solution has formed. In some embodiments, step (ii) also includes filtering the solution. In some embodiments, the elevated temperature is about 55° C. In some embodiments, step (ii) further comprises maintaining the mixture at or near the elevated temperature until Compound 1 has completely dissolved, and a clear solution has formed. In some embodiments, this time period may be about 1 minute, about 2 minutes, about 5 minutes, about 10 minutes, about 20 minutes, about 30 minutes, about 45 minutes, about 60 minutes, or about 120 minutes. In some embodiments, this time period will be less than about 180 minutes, less than about 120 minutes, less than about 60 minutes, less than about 45 minutes, or less than about 30 minutes.

The second solvent of step (iii) is MTBE or THF. In some embodiments, the second solvent is MTBE. Step (iii) may optionally include adding a seed crystal of Form II, either before or after the second solvent addition.

The crystallizing temperature of step (iv) is no more than about 35° C., less than about 30° C., less than about 25° C., less than about 20° C., less than about 15° C., less than about 10° C., or less than about 5° C. In some embodiments, the crystallizing temperature is about 25° C.

The cooling of step (iv) generally occurs over an extended time period. In some embodiments, the cooling time of step (iv) is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, or at least about 180 minutes. In some embodiments, the cooling time is about 45 minutes to about 90 minutes. In some embodiments, the crystallization/holding time period of step (iv) is at least about 20 minutes, at least about 30 minutes, at least about 45 minutes, at least about 60 minutes, at least about 75 minutes, at least about 90 minutes, at least about 105 minutes, at least about 120 minutes, or at least about 150 minutes. In some embodiments, the time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour.

The isolation step of step (v) is substantially similar to steps (vi) and (vii) of the Form I process.

An aspect of the invention is the crystalline form of Compound 1 which is hydrated and characterized by having a melting point of about 253° C., and an aqueous solubility of about 5.5 mg/mL at 25° C. ("Form II"). An embodiment of the invention is the crystalline form of Compound 1 which has an XRPD pattern that comprises peaks at 4.2, 5.6, 8.4, 17.8, and 19.8 degrees, ±0.5, ±0.2, or ±0.1 degrees, 2θ, wherein said XRPD pattern is made using Cu Kα radiation. An embodiment of the invention is the crystalline form of Compound 1 wherein the XRPD pattern further comprises a peak at 12.7 degrees, ±0.5, ±0.2, or ±0.1 degrees, 2θ. An embodiment of the invention is the crystalline form of Compound 1 having an XRPD pattern which is substantially similar to the pattern of FIG. 2.

An aspect of the invention is the method for making Form II, comprising contacting a solid form of Compound 1 with a mixture of water and a solvent selected from the group consisting of isopropanol, tetrahydrofuran, acetone, and ethyl acetate, or a combination thereof, for a period of time sufficient to produce Form II. In one embodiment, the solvent is ethyl acetate. In another embodiment, the solvent is methanol. In another embodiment, the method further comprises adding MIBK to the solvent.

C. Form III:

(A) Compound 1, in any solid form, is converted to Form III in the following process. Compound 1 is (i) contacted with an organic solvent, (ii) heated and held for a first period of time, (iii) a second solvent is added, (iv) the mixture is cooled and held for a second period of time to crystallize, and (v) the resulting solid is isolated to provide Compound 1 as pure crystalline Form III.

In some embodiments, the organic solvent of step (i) is MeOH. In some embodiments, the organic solvent contains less than about 10% water. In some embodiments, the organic solvent comprises no more than about 10% water, no more than about 8%, no more than about 5%, no more than about 2%, no more than about 1%, or no more than about 0.1% water.

The elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the solvent mixture, or no more than about 80° C., no more than about 75° C., no more than about 70° C., no more than about 60° C., no more than about 55° C., no more than about 50° C., no more than about 45° C., no more than about 40° C., or no more than about 35° C. In some embodiments, the elevated temperature is about 55° C. In some embodiments, step (ii) further comprises maintaining the mixture at or near the elevated temperature until the Compound 1 has completely dissolved, and a clear solution has formed. In some embodiments, step (ii) also includes filtering the solution. In some embodiments, the elevated temperature is about 55° C. In some embodiments, step (ii) further comprises maintaining the mixture at or near the elevated temperature until Compound 1 has completely dissolved, and a clear solution has formed. In some embodiments, this time period may be about 1 minute, about 2 minutes, about 5 minutes, about 10 minutes, about 20 minutes, about 30 minutes, about 45 minutes, about 60 minutes, or about 120 minutes. In some embodiments, this time period will be less than about 180 minutes, less than about 120 minutes, less than about 60 minutes, less than about 45 minutes, or less than about 30 minutes.

In some embodiments, the second solvent of step (iii) is acetonitrile ($CH_3CN$). The ratio of acetonitrile to MeOH solution is at least about 1:1, at least about 1:2, at least about 1:3, at least about 1:4, at least about 1:5, at least about 1:7, at least about 1:10, at least about 1:20, at least about 1:30, at least about 1:40, or at least about 1:50. Step (iii) may optionally include adding a seed crystal of Form III, either before or after the second solvent addition.

The crystallizing temperature of step (iv) is no more than about 35° C., less than about 30° C., less than about 25° C., less than about 20° C., less than about 15° C., less than about 10° C., or less than about 5° C. In some embodiments, the crystallizing temperature is about 25° C. The cooling occurs over an extended time period. In some embodiments, the cooling time of step (iv) is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, or at least about 180 minutes. In some embodiments, the cooling time is about 45 minutes to about 90 minutes. In some embodiments, the crystallization/holding time period of step iv is at least about 20 minutes, at least about 30 minutes, at least about 45 minutes, at least about 60 minutes, at least about 75 minutes, at least about 90 minutes, at least about 105 minutes, at least about 120 minutes, or at least about 150 minutes. In some embodiments, the time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour.

The isolation step of step (v) is substantially similar to steps (vi) and (vii) of the Form I process.

(B) Form III may also be produced by an alternate process. Compound 1 is (i) contacted with an organic solvent, (ii) heated and held for a first period of time, (iii) the solvent is removed rapidly under reduced pressure, and (iv) the resulting solid is isolated to provide Compound 1 as pure crystalline Form III. In some embodiments, the organic solvent of step (i) is MeOH, or a mixture of MeOH and DCM. In some embodiments, the organic solvent is MeOH. In some embodiments, the organic solvent is a mixture of MeOH and DCM. In some embodiments, the ratio of MeOH to DCM is about 1:1. In some embodiments, the organic solvent contains less than about 10% water. In some embodiments, the organic solvent comprises no more than about 10% water, no more than about 8%, no more than about 5%, no more than about 2%, no more than about 1%, or no more than about 0.1% water.

The elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the solvent mixture, or no more than about 80° C., no more than about 75° C., no more than about 70° C., no more than about 60° C., no more than about 55° C., no more than about 50° C., no more than about 45° C., no more than about 40° C., or no more than about 35° C. In some embodiments, the elevated temperature is about 55° C. In some embodiments, step ii further comprises maintaining the mixture at or near the elevated temperature until the Compound 1 has completely dissolved, and a clear solution has formed. In some embodiments, step (ii) also includes filtering the solution. In some embodiments, the elevated temperature is about 55° C. In some embodiments, this time period may be about 1 minute, about 2 minutes, about 5 minutes, about 10 minutes, about 20 minutes, about 30 minutes, about 45 minutes, about 60 minutes, or about 120 minutes. In some embodiments, this time period will be less than about 180 minutes, less than about 120 minutes, less than about 60 minutes, less than about 45 minutes, or less than about 30 minutes.

The solvent removal of step (iii) is performed rapidly, under reduced pressure. The pressure may be less than about 700 mmHg, less than about 600 mmHg, less than about 500 mmHg, less than about 400 mmHg, less than about 350 mmHg, less than about 300 mmHg, less than about 250 mmHg, less than about 200 mmHg, less than about 150 mmHg, less than about 100 mmHg, or less than about 50 mmHg. The rapid solvent removal is performed in less than about 30 minutes, less than about 20 minutes, less than about 15 minutes, less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, less than about 1 minutes.

The isolation step of step (iv) is substantially similar to steps (vi) and (vii) of the Form I process.

An aspect of the invention is the crystalline form of Compound 1 which is not anhydrous, and characterized by having a melting point of about 249° C., and an aqueous solubility of about 7.2 mg/mL at 25° C. ("Form III"). An embodiment of the invention is the crystalline form of Compound 1 which has an XRPD pattern that comprises peaks at 7.7, 10.7, 20.1, 23.7, and 24.3 degrees, ±0.5, ±0.2, or ±0.1 degrees, 2θ, wherein said XRPD pattern is made using Cu Kα radiation. An embodiment of the invention is the crystalline form of Compound 1 wherein the XRPD pattern further comprises peaks at 18.5 and 26.5 degrees, ±0.5, ±0.2, or ±0.1 degrees, 2θ. An embodiment of the invention is the crystalline form of Compound 1 having an XRPD pattern which is substantially similar to the pattern of FIG. 3.

An aspect of the invention is the method for making Form III, by contacting any solid form of Compound 1 with a solvent comprising acetonitrile for a period of time sufficient to produce Form III. An embodiment of the invention is the method wherein the solvent comprises less than about 10% water. An embodiment of the invention is the method wherein the solvent comprises less than about 5% water. An embodiment of the invention is the method wherein the solvent comprises less than about 1% water.

D. Form IV:

(A) Compound 1, in any solid form, is converted to Form IV in the following process. Compound 1 is (i) contacted with an organic solvent, (ii) heated and held for a first period of time, (iii) a second solvent is added, (iv) the mixture is cooled and held for a second period of time to crystallize, and (v) the resulting solid is isolated to provide Compound 1 as pure crystalline Form IV.

In some embodiments, the organic solvent of step (i) is MeOH. In some embodiments, the organic solvent contains less than about 5% water, no more than about 2%, no more than about 1%, or no more than about 0.1% water.

The elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the solvent mixture, or no more than about 80° C., no more than about 75° C., no more than about 70° C., no more than about 60° C., no more than about 55° C., no more than about 50° C., no more than about 45° C., no more than about 40° C., or no more than about 35° C. In some embodiments, the elevated temperature is about 55° C. In some embodiments, step (ii) further comprises maintaining the mixture at or near the elevated temperature until the Compound 1 has completely dissolved, and a clear solution has formed. In some embodiments, step (ii) also includes filtering the solution. In some embodiments, the elevated temperature is about 55° C. In some embodiments, step (ii) further comprises maintaining the mixture at or near the elevated temperature until Compound 1 has completely dissolved, and a clear solution has formed. In some embodiments, this time period may be about 1 minute, about 2 minutes, about 5 minutes, about 10 minutes, about 20 minutes, about 30 minutes, about 45 minutes, about 60 minutes, or about 120 minutes. In some embodiments, this time period will be less than about 180 minutes, less than about 120 minutes, less than about 60 minutes, less than about 45 minutes, or less than about 30 minutes.

The second solvent of step (iii) is ethyl acetate (EtOAc), isopropyl acetate, MEK, or MIBK. In some embodiments, the second solvent is ethyl acetate (EtOAc), isopropyl acetate, MEK, or MIBK. In some embodiments, the second solvent is EtOAc. In some embodiments, the second solvent is MEK. In some embodiments, the second solvent is MIBK.

The ratio of second solvent to MeOH solution (of step (i)) is at least 0.1:1, at least about 0.2:1, at least about 0.3:1, at least about 0.4:1, at least about at least about 0.5:1, at least about 1:1, at least about 1:2, at least about 1:3, at least about 1:4, at least about 1:5, at least about 1:7, at least about 1:8, at least about 1:9, at least about 1:10, at least about 1:20, at least about 1:30, at least about 1:40, or at least about 1:50.

Step (iii) may optionally include adding a seed crystal of Form IV, either before or after the second solvent addition.

The crystallizing temperature of step (iv) is no more than about 35° C., less than about 30° C., less than about 25° C., less than about 20° C., less than about 15° C., less than about 10° C., or less than about 5° C. In some embodiments, the crystallizing temperature is about 25° C. The cooling occurs over an extended time period. In some embodiments, the cooling time of step (iv) is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, or at least about 180 minutes. In some embodiments, the cooling time is about 45 minutes to about 90 minutes. In some embodiments, the crystallization/holding time period of step (iv) is at least about 20 minutes, at least about 30 minutes, at least about 45 minutes, at least about 60 minutes, at least about 75 minutes, at least about 90 minutes, at least about 105 minutes, at least about 120 minutes, or at least about 150 minutes. The time period is less than about 72 hours, less than about 48 hours, less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour.

The isolation step of step (v) is substantially similar to steps (vi) and (vii) of the Form I process.

An aspect of the invention is the crystalline form of Compound 1 which is characterized by having a melting point of about 251° C. ("Form IV"). An embodiment of the invention is the crystalline form of Compound 1 which has an XRPD pattern that comprises peaks at 18.5, 19.6, and 23.7 degrees, ±0.5, ±0.2, or ±0.1 degrees, 2θ, wherein said XRPD pattern is made using Cu Kα radiation. An embodiment of the invention is the crystalline form of Compound 1 wherein the XRPD pattern further comprises a peak at 24.6 degrees, ±0.5, ±0.2, or ±0.1 degrees, 2θ. An embodiment of the invention is the crystalline form of Compound 1 having an XRPD pattern which is substantially similar to the pattern of FIG. 4.

E. Form V—Amorphous:

Compound 1, in any solid form, is converted to Form V in the following process. Compound 1 is (i) contacted with an aqueous solvent, (ii) heated and held for a first period of time, (iii) the solution is frozen and lyophilized, and (iv) the resulting solid is isolated to provide Compound 1 as pure amorphous Form V.

In some embodiments, the aqueous solvent of step (i) is water, deionized water, or water for injection. In an embodiment of the invention, the aqueous solvent is water for injection. In an embodiment of the invention, the aqueous solvent is deionized water.

The elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the solvent mixture, or no more than about 80° C., no more than about 75° C., no more than about 70° C., no more than about 60° C., no more than about 55° C., no more than about 50° C., no more than about 45° C., no more than about 40° C., or no more than about 35° C. In an embodiment of the invention, the elevated temperature is about 45° C. In some embodiments, step (ii) further comprises maintaining the mixture at or near the elevated temperature until the Compound 1 has completely dissolved, and a clear solution has formed. In some embodiments, step (ii) also includes filtering the solution. In some embodiments, the elevated temperature is about 55° C. In some embodiments, step (ii) further comprises maintaining the mixture at or near the elevated temperature until Compound 1 has completely dissolved, and a clear solution has formed. In some embodiments, this time period may be about 1 minute, about 2 minutes, about 5 minutes, about 10 minutes, about 20 minutes, about 30 minutes, about 45 minutes, about 60 minutes, or about 120 minutes. In some embodiments, this time period will be less than about 180 minutes, less than about 120 minutes, less than about 60 minutes, less than about 45 minutes, or less than about 30 minutes.

The lyophilization step (iii) occurs over an extended time period. In some embodiments, the lyophilization time of step (iii) is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, at least about 180 minutes, at least about 3 hours, at least about 4 hours, at least about 5 hours, at least about 6 hours, at least about 7 hours, at least about 8 hours, at least about 9 hours, or at least about 10 hours. The time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour.

The isolation step of step (iv) generally requires simply collecting the amorphous solid from the lyophilization apparatus.

An aspect of the invention is the amorphous form of Compound 1 which is characterized by having a melting point of about 240° C., and an aqueous solubility of about 7.1 mg/mL at 25° C. ("Form V"). An embodiment of the invention is the amorphous form of Compound 1 having an XRPD pattern which is substantially similar to the pattern of FIG. 5.

Formulations

Compound 1 is formulated and administered according to methods known in the art. The pharmaceutical compositions containing the active ingredient may be in a form suitable for oral use, for example, as tablets, troches, lozenges, aqueous or oily suspensions, dispersible powders or granules, emulsions and self-emulsifications as described in US 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound 1 may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

Compound 1 may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

Compound 1 may be deposited within a medical device, such as a stent, and delivered to the treatment site for treatment of a portion of the body. Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), and U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz) and in WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example.

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

The polymer may be either a biostable or a bioabsorbable polymer depending on the desired rate of release or the desired degree of polymer stability. Bioabsorbable polymers that can be used include, without limitation, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinyl-pyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxypropyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like. Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning or 3D printing to place the polymer on only specific portions of the device. This coating of the device provides a uniform layer around the device which allows for improved diffusion of various analytes through the device coating.

Compound 1 can be formulated for release from the polymer coating into the environment in which the medical device is placed. For example, the compound is released in a controlled manner over an extended time frame (e.g., months) using at least one of several well-known techniques involving polymer carriers or layers to control elution. Some of these techniques were previously described in US 2004/0243225, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Another embodiment of the process includes a device having a plurality of polymer coatings, each having a plurality of diffusion coefficients. In such embodiments of the process, the release of the inhibitory agent from the polymer coating can be modulated by the plurality of polymer coatings.

The release of the inhibitory agent from the polymer coating can be controlled by modulating one or more of the properties of the polymer composition, such as the presence of one or more endogenous or exogenous compounds, or alternatively, the pH of the polymer composition. For example, certain polymer compositions can be designed to release an inhibitory agent in response to a decrease in the pH of the polymer composition. Alternatively, certain polymer compositions can be designed to release the inhibitory agent in response to the presence of hydrogen peroxide.

An aspect of the invention is a pharmaceutical composition for the treatment of a plasma kallikrein-dependent disease or condition, comprising a therapeutically effective amount of a solid form of Compound 1, and a pharmaceutically acceptable carrier, wherein the solid form of Compound 1 is Form I, Form II, Form III, Form IV, or Form V, and is substantially free of any other polymorphic form or amorphous form of Compound 1. An embodiment of the invention is a pharmaceutical composition wherein the solid form is Form I. An embodiment of the invention is a pharmaceutical composition wherein the solid form is Form II. An embodiment of the invention is a pharmaceutical composition wherein the solid form is Form III. An embodiment of the invention is a pharmaceutical composition wherein the solid form is Form IV. An embodiment of the invention is a pharmaceutical composition wherein the solid form is Form V.

An aspect of the invention is the use of a solid form of Compound 1 to make a medicament for the treatment of a plasma kallikrein-dependent disease or condition, where the solid form of Compound 1 is substantially free of any other polymorphic or amorphous form of Compound 1. Another aspect of the invention is the use of a solid form of Compound 1 for the manufacture of a medicament for the treatment of a plasma kallikrein-dependent disease or condition, where the solid form of Compound 1 is substantially free of any other polymorphic or amorphous form of Compound 1.

Administration

Pharmaceutical compositions of the invention are administered in a therapeutically effective amount by any of the modes of administration accepted for agents that serve similar utilities. The actual amount of Compound 1 administered will depend upon numerous factors such as the severity of the disease to be treated, the age and relative health of the subject, the potency of the compound used, the route and form of administration, and other factors.

An aspect of the invention is a method for treating of a plasma kallikrein-dependent disease or condition, by administering an effective amount of a pharmaceutical composition of the invention to a subject in need thereof. An embodiment of the invention is the method wherein the plasma kallikrein-dependent disease or condition is selected from diabetic macular edema, diabetic retinopathy, hereditary angioedema with C1 inhibitor deficiency, acute liver injury, inflammation, anaphylaxis, chemical-sensitized renal damage, ischemic stroke, hemorrhagic stroke, hypertension, vascular complications of hypertension, retinopathy, nephropathy, cerebrovascular edema, pulmonary hypertension, inflammation, pain, acute myocardial infarction, deep vein thrombosis, complications from fibrinolytic treatment, angina, angioedema, sepsis, arthritis, complications of cardiopulmonary bypass surgery, capillary leak syndrome, inflammatory bowel disease, diabetes, diabetic retinopathy, diabetic macular edema, diabetic nephropathy, diabetic neuropathy, age-related macular degeneration, retinal vein occlusions, brain edema, ischemia-reperfusion injury, cancer-related angiogenesis, asthma, anaphylaxis, and cerebrovascular complications of Alzheimer's Disease, Parkinson's Disease, multiple sclerosis, Central Nervous System infections, and glioblastoma multiforme.

EXAMPLES

The following examples are provided as illustration, and are not intended to limit the claimed invention. In the examples below, concentration under reduced pressure is performed at 500-600 mmHg unless otherwise specified. The following abbreviations are used: DCM=dichloromethane; MeOH=methanol; EtOH=ethanol; AcOH=acetic acid; EtOAc and AcOEt=ethyl acetate; T3P®=50% 1-propanephosphonic anhydride in EtOAc; MTBE=methyl t-butyl ether; MEK=methyl-ethyl ketone (2-butanone); MIBK=methyl-isobutyl ketone (4-methyl-2-pentanone).

X-Ray Powder Diffraction patterns were collected under ambient conditions (about 20° C.) on a PANalytical X'Pert PRO X-ray diffractometer (Malvern Panalytical, Malvern, UK) using Cu Kα radiation (45 kV, 40 mA), θ-θ goniometer, focusing mirror, divergence slit (½"), Soller slits at both incident and divergent beam (4 mm), a transmission foil sample stage (Kapton® polyimide, 12.7 μm thickness film), and a PIXcel detector. The software used for data collection was X'Pert Data Collector, version 2.2f, and the data was presented using X'Pert Data Viewer, version 1.2d. The data collection range was 2.994-35°2θ with a continuous scan speed of 0.202004° s$^{-1}$.

Differential scanning calorimetry data was collected on a PerkinElmer Pyris 6000 DSC equipped with a 45 position sample holder. The instrument was verified for energy and temperature calibration using certified indium. In the examples below, a predefined amount of the sample (0.5-3.0 mg) was placed in a pin holed aluminum pan and heated at 20° C./min from 30° C. to 350° C., or varied as experimentation dictated. A purge of dry nitrogen at 20 mL/min was maintained over the sample. The instrument control, data acquisition and analysis were performed with Pyris Software v11.1.1 revision H.

Thermo-Gravimetric Analysis data was collected on a PerkinElmer Pyris 1 TGA equipped with a 20 position auto-sampler. The instrument was calibrated using a certified weight and certified Alumel and Perkalloy for temperature. In the examples below, a predefined amount of the sample (~5 mg) was loaded onto a pre-tared aluminum crucible and was heated at 20° C./min from ambient temperature to 400° C. unless otherwise stated. A nitrogen purge at 20 mL/min was maintained over the sample. The instrument control, data acquisition and analysis were performed with Pyris Software v11.1.1 revision H.

Example 1: Synthesis of Compounds of Formula IV

Compounds of Formula IV are purchased from commercial sources, or are prepared by the methods described below, or other methods known in the art.

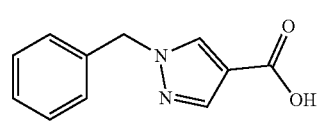

Formula IV

Ethyl 1H-pyrazole-4-carboxylate (23.5 g, 1 eq) and acetone (587 mL) was charged into a round bottom flask under N$_2$ atmosphere at 20-25° C., and the mixture was stirred for 10 minutes, followed by the addition of K$_2$CO$_3$ (70.4 g, 3 eq). the reaction mass was cooled to 0-5° C., and benzyl bromide (28.66 g, 1.1 eq) was added very slowly at 0-5° C. over a period of 15 minutes. The reaction mixture was raised to 20-25° C., then heated to 50-60° C. and maintained at that temperature for 3 hours. After the reaction was complete (monitored by HPLC), the reaction mixture was concentrated under reduced pressure at 45-50° C., quenched with 10% NaOH, and extracted with DCM (117 mL). The aqueous layer was separated, back extracted with DCM (117 mL), and the combined organic layers dried over sodium sulfate and concentrated under reduced pressure at 45-50° C. Petroleum ether or n-heptane (117 mL) was added to the concentrate and stirred for 1 hour, then filtered and dried under reduced pressure at 40-45° C. for 12 hours to yield ethyl 1-benzyl-1H-pyrazole-4-carboxylate (32.5 g).

Ethyl 1-benzyl-1H-pyrazole-4-carboxylate (30 g) and methanol (300 mL) were charged into a 3 L round bottom flask, and the resulting solution stirred for 10 minutes at 24° C. KOH (14.6 g, 2 eq) was then added, and the mixture heated to 65-70° C. and maintained for 4 hours. After the reaction was completed (as determined by HPLC), the reaction mixture was concentrated at 45-50° C. under reduced pressure to 40-60 mL. The resulting residue was dissolved in water (300 mL) and extracted with DCM (2×150 mL). The aqueous layer was separated and acidified with 6 N HCl to a pH of 2. The precipitated solids were filtered, washed with water (30 mL), and dried at 45-50° C. under reduced pressure for 12 hours to provide 1-benzyl-1H-pyrazole-4-carboxylic acid (19.5 g) as a pale brown solid, purity 99.1% by HPLC. ¹H NMR (400 MHz, DMSO-d6): δ 5.36 (s, 2H), 7.26-7.37 (m, 5H), 7.83 (s, 1H), 8.38 (s, 1H), 12.33 (broad S, 1H).

Example 2: Synthesis of Compounds of Formula III

Compounds of Formula III are prepared as described below:

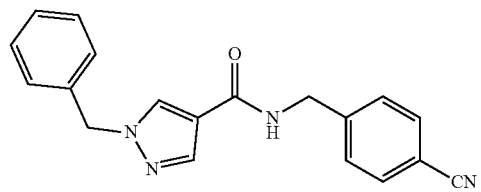

Formula III

DCM (285 mL) and 4-aminomethyl-benzonitrile hydrochloride (19.2 g, 1.2 eq) were charged into a 3 L round bottom flask, and the mixture cooled to 0° C. Triethylamine (39.4 g, 3 eq) was added at 0° C., and the resulting mixture was stirred for 30 minutes. Next, 1-benzyl-1H-pyrazole-4-carboxylic acid (19 g, 1 eq) was added at 0-5° C., and the temperature raised to 20-25° C. 1-Propanephosphonic anhydride in 50% ethyl acetate (T3P®, Spectrochem, 72 mL, 1.28 eq) was added and stirred at 20-25° C. for 3 hours. After the reaction completed, water (95 mL) was added and stirred for 10-15 minutes, and the organic layer separated. The aqueous layer was extracted again with DCM (95 mL), and the organic layers combined and washed with water (95 mL). The organic layer was dried over $Na_2SO_4$ and concentrated under reduced pressure to about 40 mL. Acetone (95 mL) was then added, and the mixture was co-distilled until only 20-30 mL remained in the pot. Water (285 mL) was then added and stirred for 1 hour at 20-25° C. The resulting solids were filtered and washed with acetone:water (1:3 v/v, 10 mL), then suction filtered and dried under reduced pressure at 45-50° C. for 12 hours to yield 1-benzyl-N-(4-cyano-benzyl)-1H-pyrazole-4-carboxamide (26.9 g, 94%) as a light brown solid, 98.51% pure by HPLC. ¹H NMR (400 MHz, DMSO-d6): δ 4.49 (d, J=5.9 Hz, 2H), 5.37 (s, 2H), 7.27-7.38 (m, 5H), 7.48 (d, J=8.1 Hz, 2H), 7.79 (d, J=8.1 Hz, 2H), 7.95 (s, 1H), 8.31 (s, 1H), 8.77 (t, J=5.9 Hz, 1H).

Example 3: Synthesis of Compounds of Formula II

Compounds of Formula II are prepared as described below:

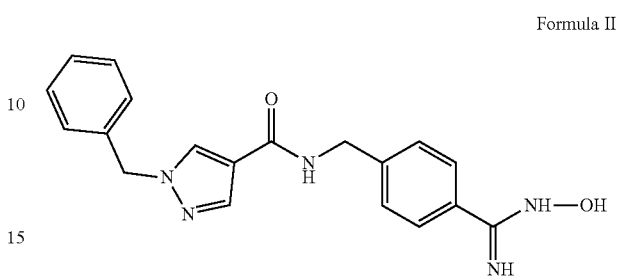

Formula II

Ethanol (250 mL) and 1-benzyl-N-(4-cyanobenzyl)-1H-pyrazole-4-carboxamide (25 g) were charged in a 1 L round bottom flask under nitrogen atmosphere at 20-25° C. Hydroxylamine hydrochloride (16.3 g, 3 eq) and triethylamine (24.64 g, 3 eq) were added to the reaction mixture at 20-25° C. The mixture was then heated to 60-65° C., and maintained at that temperature for 7 hours. After the reaction was complete, the mixture was concentrated to about 30-50 mL under reduced pressure at 45-50° C. Water (250 mL) was then added and stirred at ambient temperature for 30 minutes. The resulting solids were filtered, washed with water (125 mL), and suction filtered to dryness, then suction dried further under reduced pressure at 45-50° C. for 12 hours to yield 1-benzyl-N-(4-(N-hydroxycarbamimidoyl)benzyl)-1H-pyrazole-4-carboxamide (25.5 g, 92.3 yield) as a pale yellow solid, 95.41% pure by HPLC. ¹H NMR (400 MHz, DMSO-d6): δ 4.40 (d, J=5.9 Hz, 2H), 5.34 (s, 2H), 5.76 (broad s, 2H), 7.25-7.37 (m, 7H), 7.61 (d, J=8.2 Hz, 2H), 7.91 (s, 1H), 8.27 (s, 1H), 8.63 (t, J=5.9 Hz, 1H), 9.57 (broad s, 1H).

Example 4: Synthesis of Compounds of Formula I

Compounds of Formula I are prepared as described below:

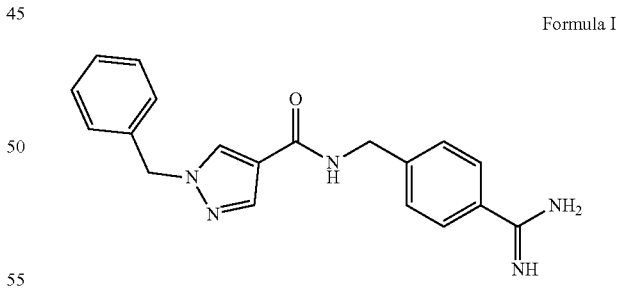

Formula I

Acetic acid (2100 g) and 1-benzyl-N-(4-(N-hydroxycarbamimidoyl)benzyl)-1H-pyrazole-4-carboxamide (200 g) were stirred at 25° C. for 10-15 minutes in a hydrogenator.
Raney nickel (40 g) and water (1 volume) were slurried in a flask, then allowed to settle for 5 minutes. The water was decanted, and another volume of water added, slurried, allowed to settle for 5 minutes, and decanted. Acetic acid (1 volume) was added, the mixture slurried for 10 minutes, then allowed to settle for 5 minutes and decanted. The Raney nickel together with acetic acid (1 volume) were then charged into the hydrogenator. The reaction mixture was heated to 60° C., and hydrogen applied (10 Kg pressure) for 30 minutes. The resulting mixture was allowed to cool to ambient temperature, and the resulting solids suction filtered for 30 minutes on Celite®. The solids were washed with MeOH (784 g), concentrated to 1-2 volumes, and charged with EtOAc (2 L). The mixture was stirred for 1 hour at 25° C., then suction filtered, washed with EtOAc (400 g), and suction dried for 2 hours. The product was further dried under reduced pressure (<300 mmHg) at 25° C. for 2 hours at 25° C., followed by drying under reduced pressure (<300 mmHg) at 45° C. for 12 hours to yield 1-benzyl-N-(4-carbamimidoylbenzyl)-1H-pyrazole-4-carboxamide acetate (220 g) as a crude product.

Example 5: Purification

The dried product (219 g) was cooled to 25° C., and charged into a round bottom flask with water (2190 mL) and stirred for 10 minutes to form a slurry. The slurry was heated to 55° C. over 20 minutes, stirred for an hour at that temperature, cooled to 25° C. over 20 minutes with stirring, and stirred for an additional 30 minutes at 25° C. The solids were filtered, washed with water (220 mL), and suction dried for 2 hours. The product was dried again under reduced pressure (<300 mmHg) at 45° C. for 12 hours, then cooled to 25° C. and charged into a round bottom flask. To this was added absolute ethanol (1250 g) and acetic acid (183 g), and the mixture heated to reflux temperature (75° C.) over 30 minutes, and maintained at reflux for 30 minutes. The mixture was then slowly cooled to 25° C. over 30 minutes, stirred at 25° C. for 45 minutes, filtered and washed with EtOH, then suction dried for 2 hours at 25° C. The product was then dried under reduced pressure (<300 mmHg) at 45° C. for 10 hours.

The dried product (143 g) was cooled to 25° C., and charged into a round bottom flask with absolute ethanol (1027 g) and acetic acid (150 g), and the mixture heated to reflux temperature (75° C.) over 30 minutes, and maintained at reflux for 1 hour. The mixture was then slowly cooled to 25° C. over 45 minutes, stirred at 25° C. for 45 minutes, filtered and washed with EtOH, then suction dried for 2 hours at 25° C. The product was then dried under reduced pressure (<300 mmHg) at 45° C. for 12 hours to provide purified 1-benzyl-N-(4-carbamimidoylbenzyl)-1H-pyrazole-4-carboxamide acetate (126 g, 56% yield, 99.6% pure by HPLC), having less than 30 ppm Nickel.

Example 6: Pure Crystalline Form 1

Figure 2:
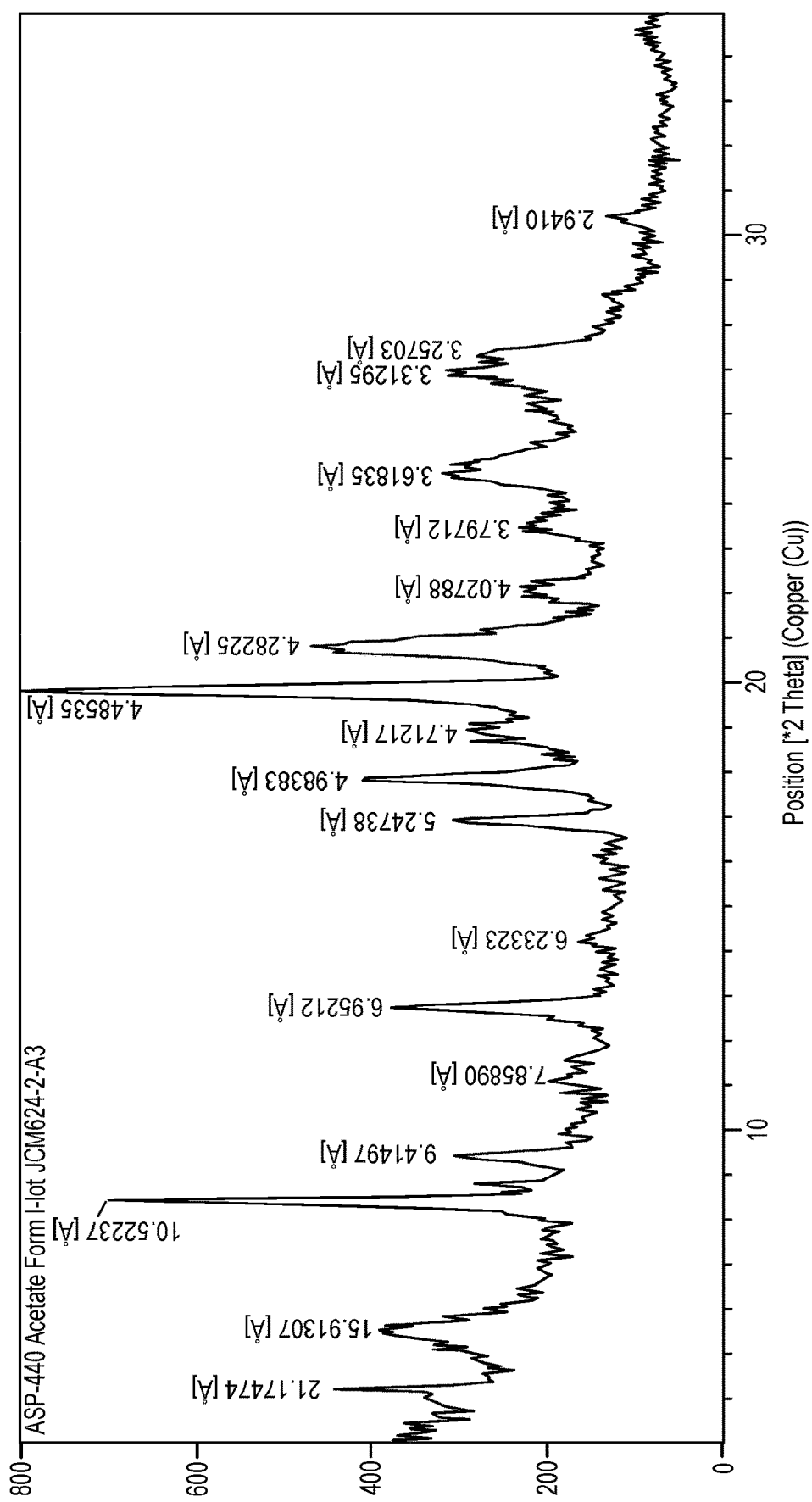
FIG. 2 depicts a powder X-ray diffraction (XRPD) pattern of crystalline Form II of Compound 1, made using Cu Kα radiation.

A mixture of crude 1-benzyl-N-(4-carbamimidoylbenzyl)-1H-pyrazole-4-carboxamide acetate (Compound 1, 10 g) in MeOH (450 mL) was charged into a 2 L round bottom flask, and the mixture heated to 50-55° C. to obtain a clear solution. The solution was maintained at 50-55° C. for 30 minutes, filtered, and charged to a reactor at 50-55° C. MTBE (450 mL) was slowly added at 50-55° C., and the mixture cooled to 25° C. over 1 hour. A white suspension was observed with cooling. MTBE (450 mL) was added slowly at 20-25° C., and the resulting mixture was stirred for 16 hours, filtered, and washed with MTBE (10 mL). The product was dried under reduced pressure at 50-55° C. for 24 hours to provide pure 1-benzyl-N-(4-carbamimidoylbenzyl)-1H-pyrazole-4-carboxamide acetate (8.25 g, 82.5% yield) in the anhydrous crystalline polymorphic form ("Form 1") as an off-white solid. The product purity was >99% by HPLC, and contained less than 14.5 ppm nickel.
$^1$H NMR (300 MHz, DMSO-d6): δ 1.71 (s, 3H), 4.47 (d, J=5.4 Hz, 2H), 5.36 (s, 2H), 7.26-7.37 (m, 5H), 7.46 (d, J=7.8 Hz, 2H), 7.74 (d, J=7.8 Hz, 2H), 7.92 (s, 1H), 8.29 (s, 1H), 8.77 (broad s, 1H), 10.34 (broad s, 3H). $^{13}$C NMR (75 MHz, DMSO-d6): δ 24.7, 41.7, 55.0, 118.4, 127.4 (2C), 127.5 (2C), 127.8 (2C), 128.2 (2C), 128.6 (2C), 131.6, 136.8, 145.2, 161.8, 165.7, 176.5. An X-ray powder diffraction (XRPD) pattern included peaks at 10.0, 18.1, 18.6, 20.1, and 23.9 degrees, ±0.5, ±0.2, or ±0.1 degrees, 2θ, (Cu Kα radiation), consistent with the XRPD pattern of FIG. 1. Thermal examination revealed a simple thermal profile with only the main melt endotherm at 251° C. on the DSC thermograph, and a single weight reduction indicative of acetate loss (FIG. 2).

Example 7: Pure Crystalline Form 2

(A) Crystallization: Compound 1 (53 mg) was weighed into a vial, dissolved in 3:1 MeOH:H$_2$O (1 mL, 20 vol.) at 55° C. and clarified into a crystallization tube at 50° C.

The solution was charged with MTBE (1 mL), and held at 50° C. for about 10 minutes. The solution developed a suspension within 3 minutes of MTBE addition. The mixture was cooled to 25° C. over about 1 hour, and equilibrated for a further 1 hour, but remained as a suspension. The solid was isolated by filtration and dried in vacuo at 50° C. for about 16 hours to yield an off-white solid with a recovery of 62.3%. An X-ray powder diffraction (XRPD) pattern included peaks at 4.2, 5.6, 8.4, 17.8, and 19.8 degrees, ±0.5, ±0.2, or ±0.1 degrees, 2θ, (Cu Kα radiation), consistent with the XRPD pattern of FIG. 2.

(B) Seeded Crystallization: Compound 1 (1.008 g) was weighed into a vessel and 3:1 MeOH:H$_2$O (22 mL, 22 vol.), was charged. The mixture was heated to 55° C. to achieve dissolution. The solution was clarified and charged to a vessel at 50° C. To the solution was added a Form II seed (about 10 mg), and observed to persist.

Figure 9:
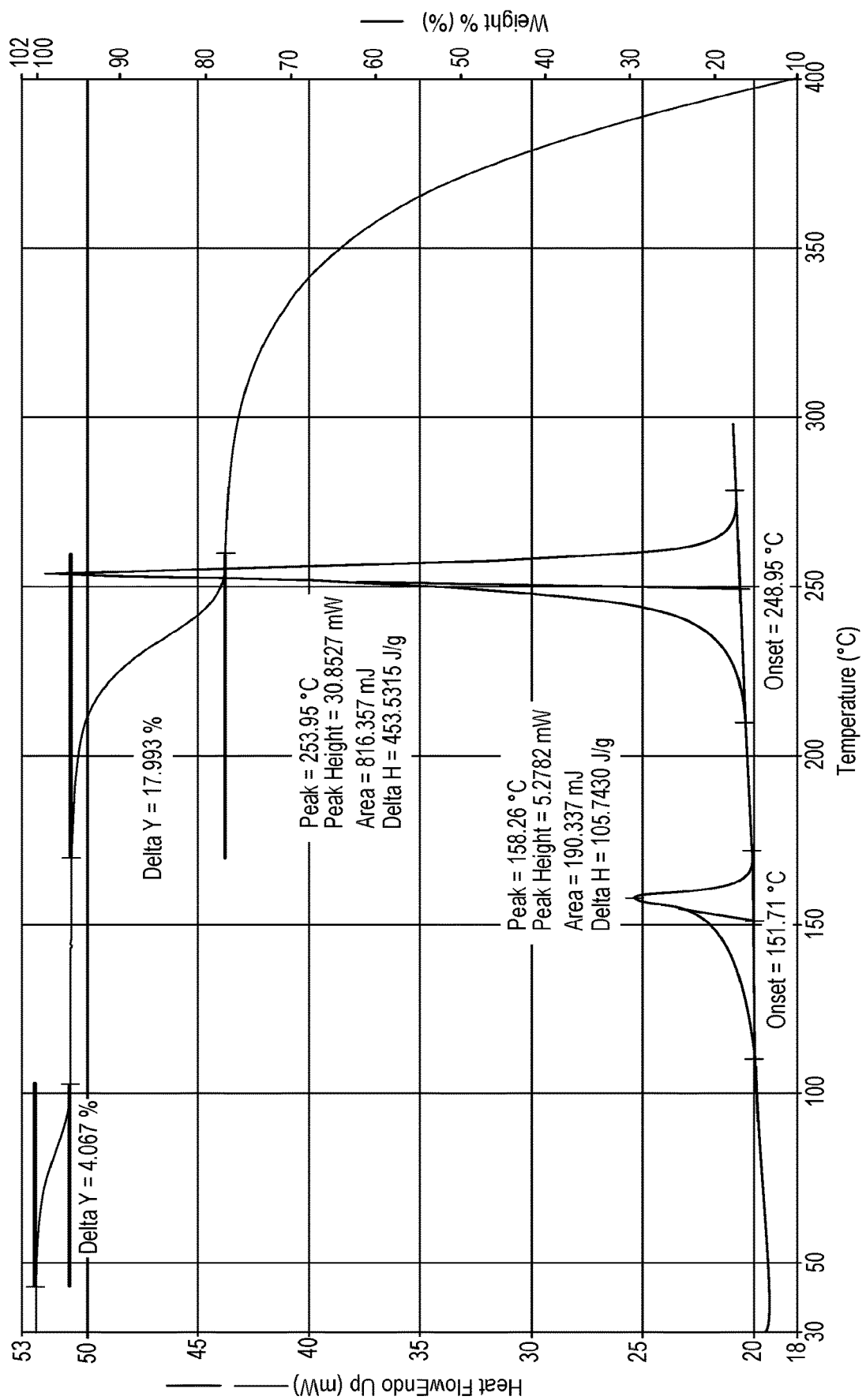
FIG. 9 depicts a DSC and TGA thermograph overlay of Compound 1, Form II.

MTBE (22 mL, 22 vol.) was charged into the vessel, and the mixture was cooled to 25° C. over about 1 hour. A fine, off-white suspension was observed to mature with cooling. The mixture was equilibrated for a further 45 minutes, and additional MTBE (22 mL, 22 vol.) was charged. The suspension was equilibrated at 25° C. for a further 16.5 hours. The solid was isolated by filtration and dried in vacuo at 50° C. for about 23.5 hours to give a white free-flowing powder solid with a yield of 73.5%. An X-ray powder diffraction (XRPD) pattern included peaks at 4.2, 5.6, 8.4, 17.8, and 19.8 degrees, ±0.5, ±0.2, or ±0.1 degrees, 2θ, (Cu Kα radiation), consistent with the XRPD pattern of FIG. 2. Thermal examination (FIG. 9) revealed a DSC thermograph typical of Form II with a significant endotherm at 158° C. prior to the main melt endotherm at 254° C. The TGA thermograph revealed a 4.067 wt % weight reduction from 40-105° C., suggesting near stoichiometric water loss, prior to the acetate loss weight reduction event Example 8: Pure Crystalline Form 3

(A) Via CH$_3$CN: Compound 1 (25 mg) was weighed into a crystallization tube, and acetonitrile (MeCN) charged in 0.1 mL (4 vol.) aliquots up to 0.5 mL (20 vol.) with immediate observations noted. The mixture was agitated via magnetic stirrer bar and heated to 50° C., and observations were noted after 4 hours. With no clear dissolution, the solvent volume was doubled to 1 mL (40 vol.) and immediate observations noted. The mixture was cooled to 25° C., and equilibrated for 65 hours. Observations were noted and half of the mixture was isolated. The mixture was heated to 50° C. and equilibrated for 6 hours before the remainder was isolated.

Figure 10:
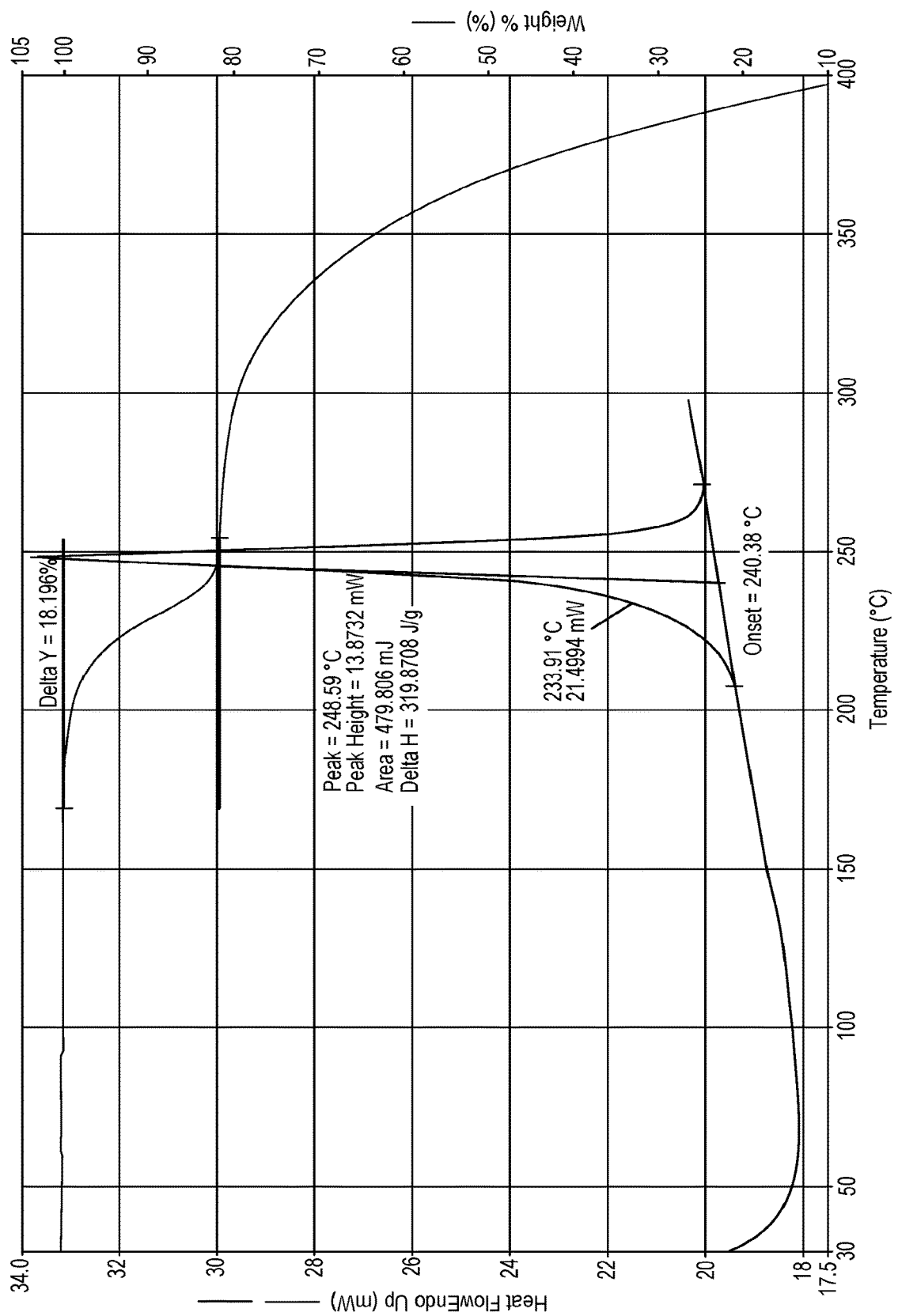
FIG. 10 depicts a DSC and TGA thermograph overlay of Compound 1, Form III.

The solids were dried in vacuo at 50° C. for 17 hours before analysis by XRPD examination. An X-ray powder diffraction (XRPD) pattern included peaks at 7.7, 10.7, 20.1, 23.7, and 24.3 degrees, consistent with the XRPD pattern of FIG. 3. Thermal examination of Form III (FIG. 10) revealed a single endotherm peaking at 249° C., with evidence of a minor shoulder at 234° C. on the DSC thermograph. There was only acetate disproportionation weight reduction by TGA at the melt.

(B) Via MeOH: Compound 1 (1.050 g) was weighed into a flask, and MeOH (50 mL, 50 vol.) was charged. The mixture was heated to 50° C. and held for 20 minutes. Dissolution was only partial, so further heating to 60° C. and additional MeOH (10 mL, 60 vol. total) was applied to achieve dissolution. The solution was clarified and reduced to dryness in vacuo, then dried further in vacuo at 50° C. for 16.5 hours to return a pink, voluminous, low-density solid with a recovery of 76.1%.

Example 9: Pure Crystalline Form 4

(A) From Form 1: Compound 1 (211 mg) was weighed into a vial, and MeOH (8.44 mL, 40 vol.) charged. The mixture was heated to 50° C. and held for 1 hour. Dissolution was only partial, so further heating was applied to achieve dissolution. The solution was clarified and charged to a crystallization tube at 50° C. in 1 mL aliquots. EtOAc was charged in 0.1 mL aliquots up to 1 mL. The mixture was cooled to 20° C. over 2 hours and equilibrated at 20° C. for a further 19.25 hours.

Figure 11:
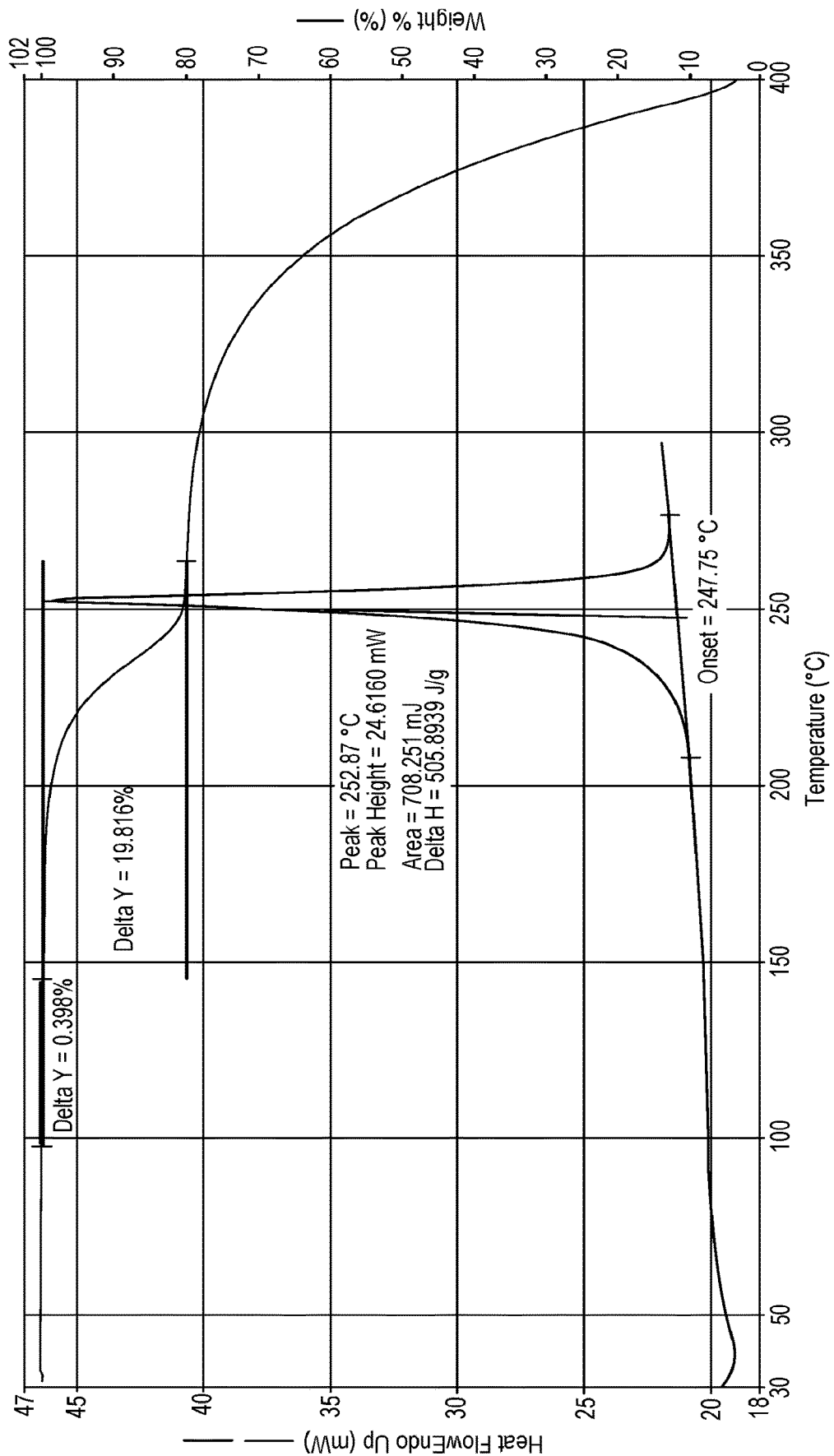
FIG. 11 depicts a DSC and TGA thermograph overlay of Compound 1, Form IV.

The solids were dried in vacuo at 50° C. for about 22.5 hours. An X-ray powder diffraction (XRPD) pattern included peaks at 18.5, 19.6, and 23.7 degrees 2θ, ±0.5, ±0.2, or ±0.1 degrees, consistent with the XRPD pattern of FIG. 4. Thermal examination of Form IV revealed a simple thermal profile (FIG. 11) with only the main melt endotherm at 253° C. on the DSC thermograph, and a minor weight reduction of about 0.40 wt % from 100-150° C. prior to the loss of acetate.

(B) From Amorphous: Amorphous Compound 1 (4×50 mg), and Form 4 (4×2 mg) were weighed into 4 crystallization tubes and 4 solvents charged (THF, EtOAc, MIBK, and MEK: 2 mL, 40 vol.). The mixtures were agitated via magnetic stirrer bar at 50° C. for about 21 hours before cooling to 25° C. The suspensions were equilibrated at 25° C. for about 7.5 hours before heating to 50° C. The suspensions were equilibrated at 50° C. for about 16 hours before cooling to 25° C., and the solids isolated by filtration.

The solids were dried in vacuo at 50° C. for about 72 hours. The solids recovered from THF or EtOAc were demonstrated by XRPD to be Form 1, while the solids recovered from MIBK or MEK were shown to be Form 4.

Example 10: Pure Amorphous Form 5

Compound 1 (495 mg) was weighed into a flask with deionized water (250 mL), and dissolution achieved with agitation at 45° C. The solution was clarified into a 3 L flask, frozen and lyophilized over about 9 hours. A white, voluminous solid was isolated, with a recovery of about 83.6%. Examination by XRPD showed that the solid was predominantly amorphous, but with traces of Form II present.

Figure 5:
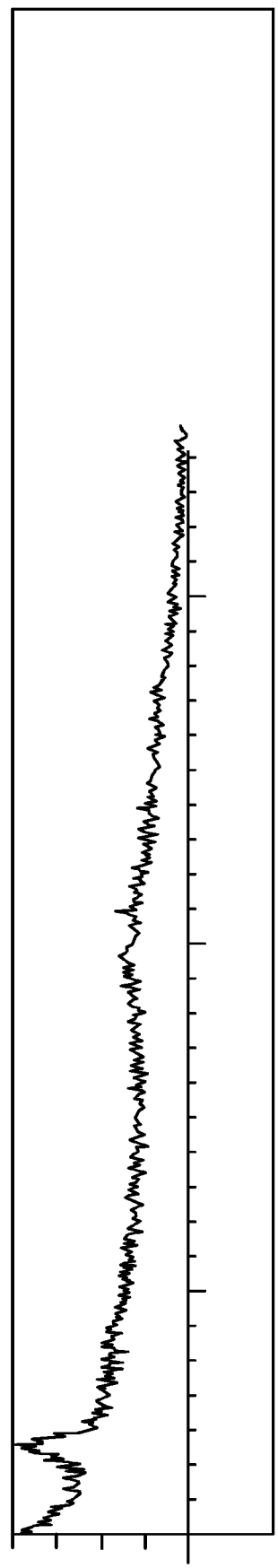
FIG. 5 depicts a powder X-ray diffraction (XRPD) pattern of amorphous Form V of Compound 1, made using Cu Kα radiation.
Figure 12:
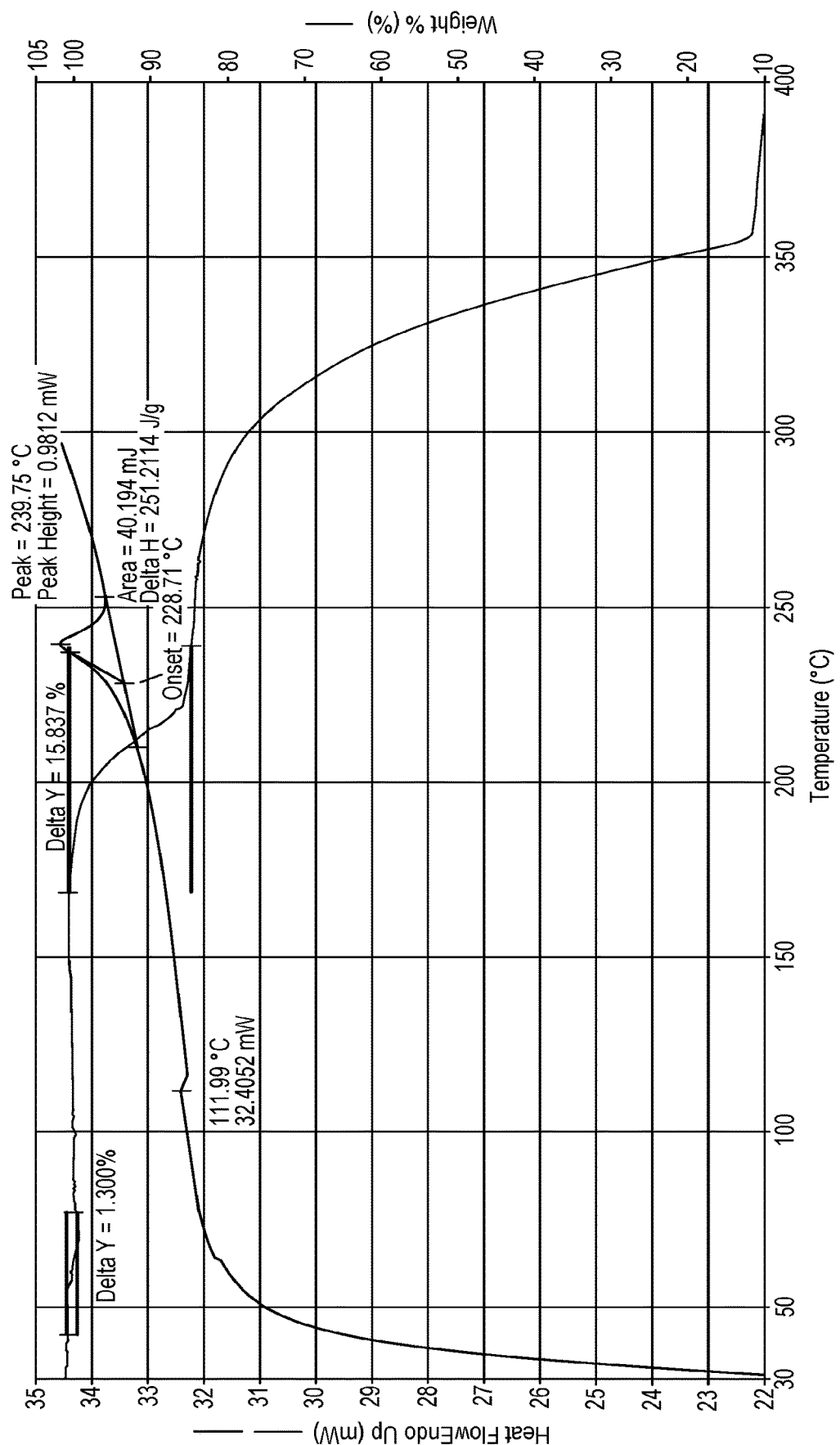
FIG. 12 depicts a DSC and TGA thermograph overlay of amorphous Compound 1, Form V.

The process above was repeated, lyophilizing the solid over about 6.25 hours, to yield a white, voluminous solid with a recovery of 70.5%. Examination by XRPD showed that the material is predominantly amorphous (FIG. 5). Thermal examination (FIG. 12) revealed a minor endothermic event at about 112° C., similar to Form II, and a main endotherm with an onset and peak at about 229° C. and 240° C., slightly reduced compared to Form II. A weight reduction of 1.300 wt % from 40-80° C. was observed which was predominantly residual surface moisture. A second significant weight reduction of 15.837 wt % from 170-240° C., corresponding with the melt, indicated acetate loss (15.01 wt %), and potentially further entrapped water loss or a minor degradation event leading into the onset of decomposition from 250° C.

Example 11: Compression and Grinding Stability

The manufacturing process for solid dosage forms can require high compression and/or grinding, which may cause a change in crystal structure for some compounds. Compound 1 Form I and Form II were subjected to compression under $11\times10^5$N force for about 25-28 hours to assess the impact of compression upon the form stability of these crystalline forms.

Figure 6:
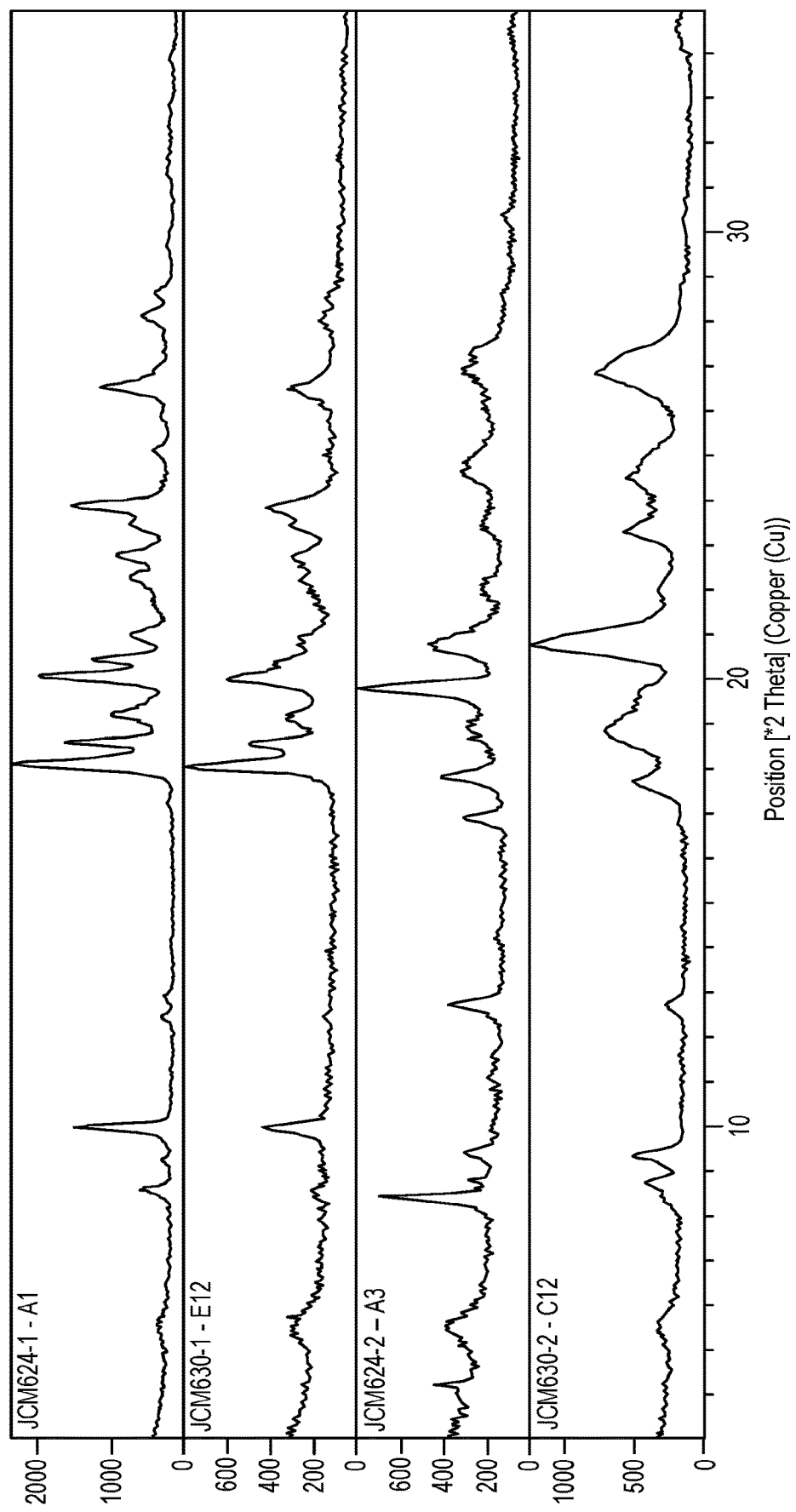
FIG. 6 depicts powder X-ray diffraction (XRPD) patterns of crystalline Forms I and Form II before and after compression at under $11 \times 10^5$ N force for about 25-28 hours. The first and third traces show the XRPD patterns for Form I and Form II, respectively, prior to compression. Traces 2 and 4 show the XRPD patterns for Form I and Form II, respectively, following compression.

XRPD examination revealed a subtle reduction in diffraction resolution of Form I. Examination of Form II revealed a significant change in the diffraction pattern to a pattern of reduced crystallinity, as shown in FIG. 6. Thermal examination of Form I revealed no change in the TGA thermograph following compression. There was a reduction in the intensity and temperature of the melt endotherm in the DSC thermograph following compression. Thermal examination of Form II revealed a slight increase in the water content by the TGA thermograph, however, this may have been due to aging of the sample following isolation rather than the act of compression. The DSC thermograph revealed a reduction in the intensity, but increase of the temperature of the main melt endotherm, and the addition of a significant endotherm at about 150° C. following compression.

Samples of both Form I and Form II (about 100 mg each) were subjected to grinding operations to assess the impact on solid form and observed microscopy. It was of interest to note whether amorphous content was generated, and to review the impact upon water content for the batches, especially with regards to Form II hydrate.

Figure 7:
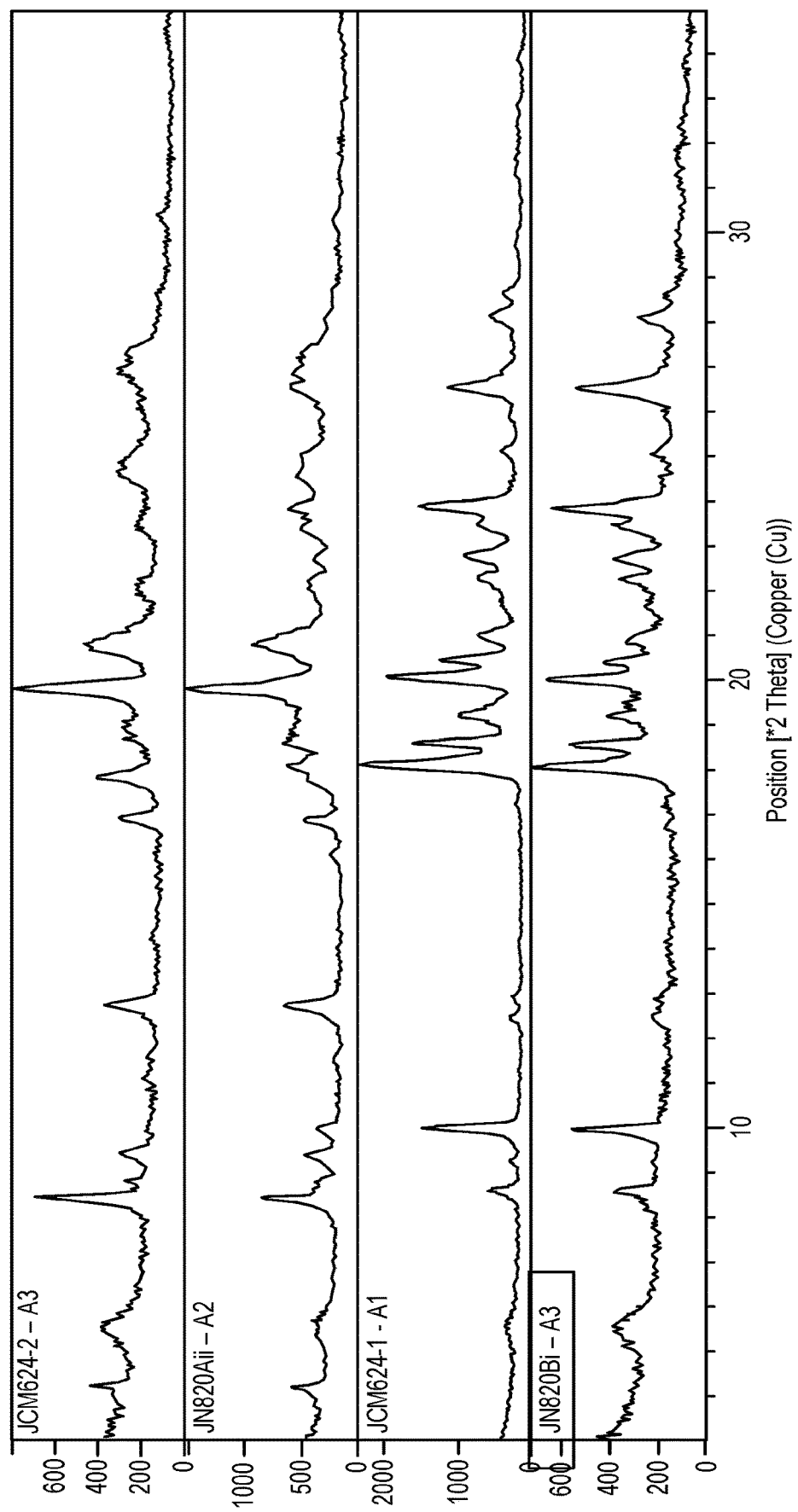
FIG. 7 depicts powder X-ray diffraction (XRPD) patterns of crystalline Forms I and Form II before and after grinding. The first and third traces show the XRPD patterns for Form I and Form II, respectively, prior to grinding. Traces 2 and 4 show the XRPD patterns for Form I and Form II, respectively, following grinding.
Figure 8:
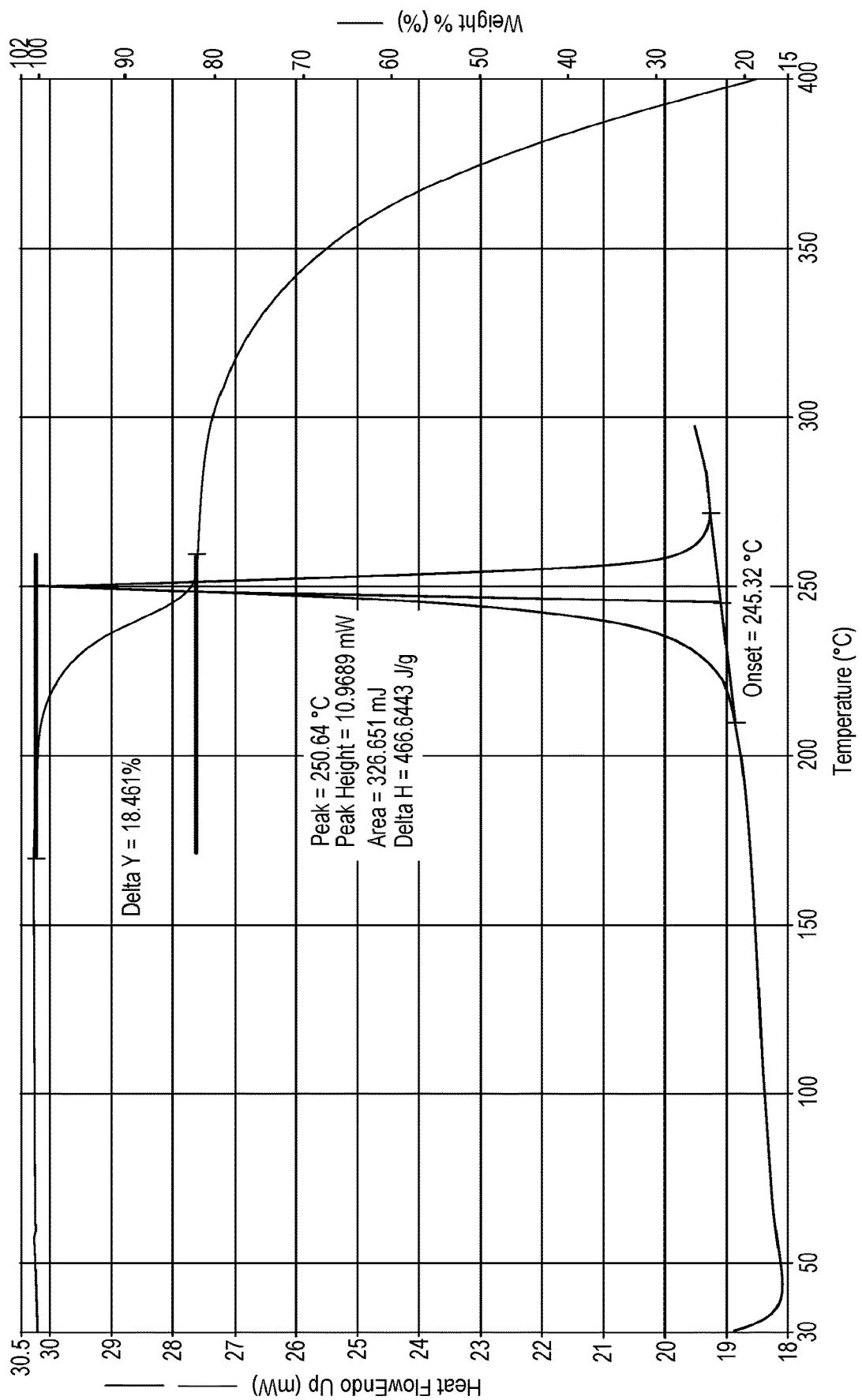
FIG. 8 depicts a DSC and TGA thermograph overlay of Compound 1, Form I.

The data sets for both samples post-grinding were clear in that no change was induced either thermally or crystallographically. Form II displayed a minor alteration in reflection resolution and intensity, but neither sample was indicative of amorphous content thermally or via XRPD compared to the input, as shown in FIG. 7. The most significant change was that, as for compressed materials, Form II had gained in water content to 3.93 wt % (from 2.76 wt %) at point of production, and was in keeping with the hydrate anticipated.

Microscopy examination was performed where both samples were compared to their original states. Post grinding, both samples dispersed extremely well under silicon oil. Form II retained more particulates of 5-10 μm size, but the majority of solids were <5 μm. Form I was broken down into a very fine and evenly dispersed solid of predominantly <5 μm particulates (most 1-2 μm), which was anticipated given the relatively small particle size observed in the input lot. In summary, Form I demonstrated superior stability to hydrated Form II under manual stress.

What is claimed is:

1. An amorphous form of 1-benzyl-N-(4-carbamimidoylbenzyl)-1H-pyrazole-4-carboxamide acetate, Form V, characterized by an XRPD pattern that is substantially similar to the pattern in FIG. 5.

2. The amorphous form of claim 1, further characterized by a melting point of about 240° C.

3. The amorphous form of claim 1, further characterized by an aqueous solubility of about 7.1 mg/mL in water at 25° C.

4. The amorphous form of claim 1, further characterized by a weight reduction of about 1.300 wt % when heated from 40-80° C.

5. The amorphous form of claim 1, further characterized by a weight reduction of about 15.837 wt % when heated from 170-240° C.

6. The amorphous form of claim 1, characterized by a thermal gravimetric analysis (TGA) thermogram substantially in accordance with FIG. 12.

7. The amorphous form of claim 1, characterized by a differential scanning calorimetry thermogram (DSC) substantially in accordance with FIG. 12.

8. A pharmaceutical composition comprising the amorphous form of claim 1, and a pharmaceutically acceptable carrier.

9. A method for treating of a plasma kallikrein-dependent disease or condition, comprising: administering an effective amount of the crystalline form of claim 1.

10. The method of claim 9, wherein the plasma kallikrein-dependent disease or condition is selected from the group consisting of:
diabetic macular edema, diabetic retinopathy, hereditary angioedema with C1 inhibitor deficiency, acute liver injury, inflammation, anaphylaxis, chemical-sensitized renal damage, ischemic stroke, hemorrhagic stroke, hypertension, vascular complications of hypertension, retinopathy, nephropathy, cerebrovascular edema, pulmonary hypertension, inflammation, pain, acute myocardial infarction, deep vein thrombosis, complications from fibrinolytic treatment, angina, angioedema, sepsis, arthritis, complications of cardiopulmonary bypass surgery, capillary leak syndrome, inflammatory bowel disease, diabetes, diabetic retinopathy, diabetic macular edema, diabetic nephropathy, diabetic neuropathy, age-related macular degeneration, retinal vein occlusions, brain edema, ischemia-reperfusion injury, cancer-related angiogenesis, asthma, anaphylaxis, cerebrovascular complications of Alzheimer's Disease, Parkinson's Disease, multiple sclerosis, Central Nervous System infections, and glioblastoma multiforme.

11. The method of claim 10, wherein the disease or condition is diabetic macular edema.

* * * * *